United States Patent
Chiang et al.

(10) Patent No.: US 11,484,226 B2
(45) Date of Patent: Nov. 1, 2022

(54) HEARING TEST SYSTEM AND METHOD FOR DETERMINING CREDIBILITY OF A HEARING TEST

(71) Applicant: MERRY ELECTRONICS (SHENZHEN) CO., LTD., Guangdong (CN)

(72) Inventors: Yung-Yu Chiang, Taichung (TW); Tun-Shin Lo, Taichung (TW); Hung-Yue Chang, Taichung (TW)

(73) Assignee: MERRY ELECTRONICS (SHENZHEN) CO., LTD., Guangdong (CN)

( * ) Notice: Subject to any disclaimer, the term of this patent is extended or adjusted under 35 U.S.C. 154(b) by 557 days.

(21) Appl. No.: 16/594,083

(22) Filed: Oct. 7, 2019

(65) Prior Publication Data
US 2020/0305768 A1 Oct. 1, 2020

(30) Foreign Application Priority Data
Mar. 27, 2019 (TW) .................... 108110791

(51) Int. Cl.
*A61B 5/12* (2006.01)
*A61B 5/00* (2006.01)
*G06F 3/16* (2006.01)

(52) U.S. Cl.
CPC ............ *A61B 5/123* (2013.01); *A61B 5/7221* (2013.01); *A61B 5/7475* (2013.01); *G06F 3/165* (2013.01)

(58) Field of Classification Search
CPC ..... A61B 5/123; A61B 5/7221; A61B 5/7475; G06F 3/165
See application file for complete search history.

(56) References Cited

U.S. PATENT DOCUMENTS

| 4,284,847 A * | 8/1981 | Besserman | A61B 5/12 73/585 |
| 2006/0045281 A1* | 3/2006 | Korneluk | H04R 5/04 381/60 |
| 2013/0085411 A1* | 4/2013 | Van Tasell | A61B 5/12 600/559 |
| 2016/0338622 A1* | 11/2016 | Chen | A61B 5/121 |

* cited by examiner

*Primary Examiner* — David D Davis
(74) *Attorney, Agent, or Firm* — CKC & Partners Co., LLC

(57) ABSTRACT

A hearing test system includes a sound generating unit, an user interface, and a control unit. The sound generating unit is configured to generate a first testing sound at a frequency for a subject. The user interface is configured to receive a first feedback of the subject based on the first testing sound. The control unit is configured to determine whether the first feedback is of heard response or an unheard response. When the control unit confirms that the first feedback is of the heard response, the control unit drives the sound generating unit to generate a second testing sound based on a lower testing limit at the frequency, in which a volume of the second testing sound is less than or substantially equal to a volume of the first testing sound.

5 Claims, 21 Drawing Sheets

☐ testing sound
▢ blank stimulating sound
○ feedback of heard
✕ feedback of unheard

HEARING TEST SYSTEM AND METHOD FOR DETERMINING CREDIBILITY OF A HEARING TEST

CROSS-REFERENCE TO RELATED APPLICATION

This application claims priority to Taiwan Application Serial Number 108110791, filed Mar. 27, 2019, which is herein incorporated by reference in its entirety.

BACKGROUND

Field of Invention

The present invention relates to a hearing test system. More particularly, the present invention relates to a method for determining a credibility of a hearing test.

Description of Related Art

The so-called assistive listening device receive external sound through a microphone, and then use a digital signal processor (DSP) to filter noise or adjust the sound of the surrounding environment. Finally, a speaker transmits the filtered sound to the eardrum of the user. In this way, people with different levels of hearing impairment can easily participate in group life to improve their quality of life and maintain good interpersonal relationships.

However, in the case of hearing-impaired people, even with assistive listening device, hearing may still gradually deteriorate with age, but in the design of traditional assistive listening device, the lack of hearing function, once the assistive listening device is not adjusted correspondingly, and the assistive listening device can not properly handle the received external sounds in accordance with the user's hearing condition, which will affect the assistive hearing effect of the assistive listening device.

Furthermore, in the past, the assistive listening device can only be used for the hearing loss of the hearing aids after the hearing curve is set for the hearing impaired person, that is, the assistive listening device can no longer be provided to others of different hearing situations. Therefore, the use range of the assistive listening device has been limited, and the extensiveness is also insufficient.

SUMMARY

The invention provides a hearing test system and method for determining a credibility of a hearing test.

In some embodiments, a hearing test system includes a sound generating unit, an user interface, and a control unit. The sound generating unit is configured to generate a first testing sound at a frequency for a subject. The user interface is configured to receive a first feedback of the subject based on the first testing sound. The control unit is configured to determine whether the first feedback is of heard response or an unheard response. When the control unit confirms that the first feedback is of the heard response, the control unit selectively drives the sound generating unit to generate a second testing sound based on a lower testing limit at the frequency, in which a volume of the second testing sound is less than or substantially equal to a volume of the first testing sound.

In some embodiments, the lower testing limit equals to about 15 dB and the upper testing limit equals to about 70 dB.

In some embodiments, when the control unit confirms that the first feedback is of the heard response, if the volume of the first testing sound not equals to the lower testing limit, the volume of the second testing sound is set to be less than the volume of the first test sound.

In some embodiments, when the control unit confirms that first feedback is of the heard response, if the volume of the first testing sound equals to about the lower testing limit, the volume of the second testing sound is set to be about the volume of the first testing sound.

In some embodiments, the user interface is further configured to receive the second feedback of the subject based on the second testing sound and when the control unit confirms that the second feedback is of the heard response, the control unit is configured to stop the sound generating unit generating sound at the frequency.

In some embodiments, when the control unit confirms that the first feedback is of the unheard response, if the volume of the first testing sound is not equals to the upper testing limit, the volume of the third testing sound is set to be greater than the volume of the first testing sound.

In some embodiments, the blank stimulating sound is not performed directly after the third testing sound.

In some embodiments, when the control unit confirms that the first feedback is of the unheard response, if the volume of the first testing sound equals to about the upper testing limit, the volume of the third testing sound is set to be about the volume of the first testing sound.

In some embodiments, the user interface is further configured to receive a third feedback of the subject based on the third testing sound, and when the control unit confirms that the third feedback is of the unheard response, the control unit is configured to stop the sound generating unit generating the sound at the frequency.

In some embodiments, a method for determining a credibility of a hearing test includes sequentially generating a plurality of testing sounds of different volumes at each one of a plurality of frequencies for a subject; selectively inserting a plurality of blank stimulating sounds between the testing sounds, in which volumes of the blank stimulating sounds each equals to about zero; receiving a plurality of feedbacks of the subject respectively corresponding to the blank stimulating sounds; and generating a credibility analysis output based on the feedbacks.

In some embodiments, the selectively inserting of the blank stimulating sounds between the testing sounds is performed such that when the feedbacks of consecutive two of the testing sounds are of the heard responses, the blank stimulating sound is set to be performed selectively after consecutive two of the testing sounds.

In some embodiments, when a first number of the feedbacks of the heard response in the blank stimulating sounds is greater than a second number of the feedbacks of the unheard response in the blank stimulating sounds, the credibility analysis output is set to be of a poor reliability.

In some embodiments, the method further includes responsive to a volume usage percentage for each of the frequencies, classifying each of the frequencies into a poor reliability frequency or an acceptable reliability frequency, in which the generating of the credibility analysis output is responsive to a ratio of a first number of the reliability frequency to a second number of the acceptable reliability frequency.

In some embodiments, the classifying of each of the frequencies into the poor reliability frequency or the acceptable reliability frequency includes calculating a third number of a plurality of designed usage volumes for each of the frequencies and further calculating a fourth number of a plurality of actual usage volumes for the each of the frequencies, when the fourth number of the actual usage volumes is greater than or equal to 80% of the third number of the designed usage volumes for a corresponding one of the frequencies, the corresponding one of the frequencies is classified as the poor reliability frequency, and when the fourth number of the actual usage volumes is less than 80% of the third number of the designed usage volumes for a corresponding one of the frequencies, the corresponding one of the frequencies is classified as the acceptable reliability frequency.

In some embodiments, when a fifth number of the frequencies that are of the poor reliability frequency is greater than or equal to a sixth number the frequencies that are of the acceptable reliability frequency, the credibility analysis output is set to be of a poor reliability.

In the aforementioned configurations, a credibility of a hearing test method may be affected by a subject's improper operation of a hearing test system. Therefore, a blank stimulating sound may be inserted to verify the reliability of the data of the hearing test method, thereby preventing the subject from adjusting a hearing function of an assistive listening device by using a test result with poor reliability. As such, the accuracy of the assistive listening device can be improved.

It is to be understood that both the foregoing general description and the following detailed description are by examples, and are intended to provide further explanation of the invention as claimed.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
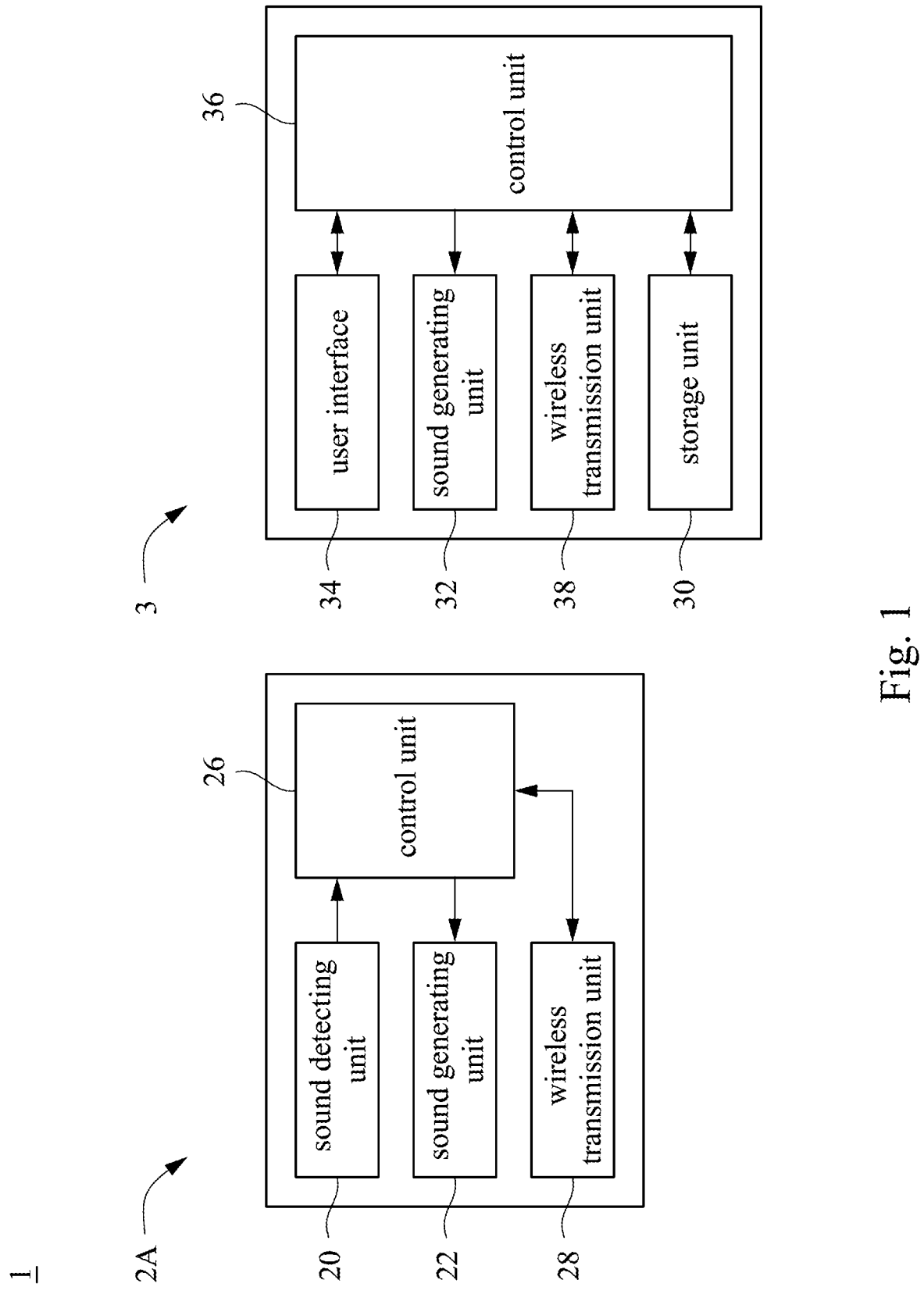
FIG. 1 illustrates a schematic diagram of a hearing test system according to some embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Reference is made to FIG. 1. FIG. 1 illustrates a schematic diagram of a hearing test system 1 according to some embodiments of the present disclosure. As shown in FIG. 1, in the embodiment, the hearing test system 1 includes an assistive listening device 2A, an assistive listening device 2B (See FIG. 12A) and an electronic device 3. In the embodiment, the electronic device 3 may be a portable mobile phone, but the present disclosure is not limited thereto. The structure and function of the components and their relationships in the hearing test system 1 are described in detail hereinafter.

In FIG. 1, the assistive listening device 2A includes a sound detecting unit 20, a sound generating unit 22, a control unit 26, and a wireless transmission unit 28. In the embodiment, the structure and function of the components and their relationships in the assistive listening device 2B shown in FIG. 12A is substantially the same as the assistive listening device 2A shown in FIG. 1, and reference may be made to the foregoing paragraphs for the related detailed descriptions and such descriptions are not provided again herein. In the embodiment, the assistive listening device 2A and the assistive listening device 2B are configured to be worn on two ears of a subject, respectively.

In the embodiment, the sound detecting unit 20 is electrically connected to the control unit 26 and is configured to detect a volume generated by the electronic device 3 or to detect a volume of an environmental noise. The sound generating unit 22 is electrically connected to the control unit 26 and is configured to general a sound. For example, the sound generating unit 22 includes a speaker and/or an audio amplifier. In the embodiment, the term of volume may also be intensity and can be expressed in decibels, sound pressure or other suitable units.

In the embodiment, the sound generating unit 22 is configured to generate testing sounds belonging to at least one testing frequency (e.g., 500 Hz, 1 kHz, 2 kHz, and/or 4 kHz) for a subject through an instruction of the control unit 26 and a control unit 36 of the electronic device 3. In some embodiments, the sound generating unit 22 is configured to generate testing sounds at each of the testing frequencies that are with volumes each in a range from about a lower testing limit TL (See FIG. 3A) to about an upper testing limit (See FIG. 3A). In the embodiment, the lower testing limit TL may be about 15 dB, and the upper testing limit TH may be about 70 dB, but the present disclosure is not limited thereto.

In some embodiments, the sound generating unit 22 may be configured to generate five sounds with different volume at each of the testing frequencies, but the present disclosure is not limited thereto. The volumes of the five different testing sounds may be designed to be about volumes A1, A2, A3, A4, and A5 from the lower testing limit TL to the upper testing limit TH in sequentially (See FIG. 3A). For example, the volume A1, A2, A3, A4, and A5 may be designed to be about 25 dB HL, 40 dB HL, 50 dB HL, 60 dB HL, and 70 dB HL, respectively, but the present disclosure is not limited thereto. In some embodiments, the intensity and quantity of the testing sound generated by the sound generating unit 22 can be designed according to actual needs at each testing frequency.

In the embodiment, the wireless transmission unit 28 is electrically connected to the control unit 26 and is configured to transmit signals to and from a wireless transmission unit 38 in the electronic device 3. In the embodiment, the wireless transmission unit 28 may be a bluetooth communication unit, but the present disclosure is not limited thereto.

In FIG. 1, the electronic device 3 includes a storage unit 30, a sound generating unit 32, an user interface 34, the control unit 36, and the wireless transmission unit 38. In the embodiment, the storage unit 30 is electrically connected to the control unit 36 and is configured to store data. The sound generating unit 32 is electrically connected to the control unit 36 and is configured to generate a sound. For example, the sound generating unit 32 includes a speaker and/or an audio amplifier.

In the embodiment, the user interface 34 is configured to receive a feedback of a subject based on a testing sound. For example, the user interface 34 may be a touch display component, but the present disclosure is not limited thereto. The control unit 36 is configured to determine whether a feedback of a subject is of heard or unheard and is further configured to determine a testing hearing threshold at a frequency based on the feedbacks. The wireless transmission unit 38 is electrically connected to the control unit 36 and is configured to transmit signals to and from wireless transmission units in the assistive listening devices 2A and 2B. In the embodiment, the wireless transmission unit 38 may be a bluetooth communication unit, but the present disclosure is not limited thereto.

It is noted that, the above-described modules can be implemented in hardware devices, software programs, firmware, or a combination thereof, and they can also be configured as electrical circuits or other suitable forms; furthermore, each module can be implemented independently or can be combined with any other modules. In addition, the present embodiment is merely a preferred embodiment of the present invention, and for the sake of brevity, not all possible combinations and variations are described. However, it is known to those who are skilled in the art that the above-described modules or elements may not be necessary. For the purpose of the invention, it may also contain other well-known modules or elements. Each module or component may be omitted or modified as needed, and there may be any other modules or components between any two modules.

Figure 2:
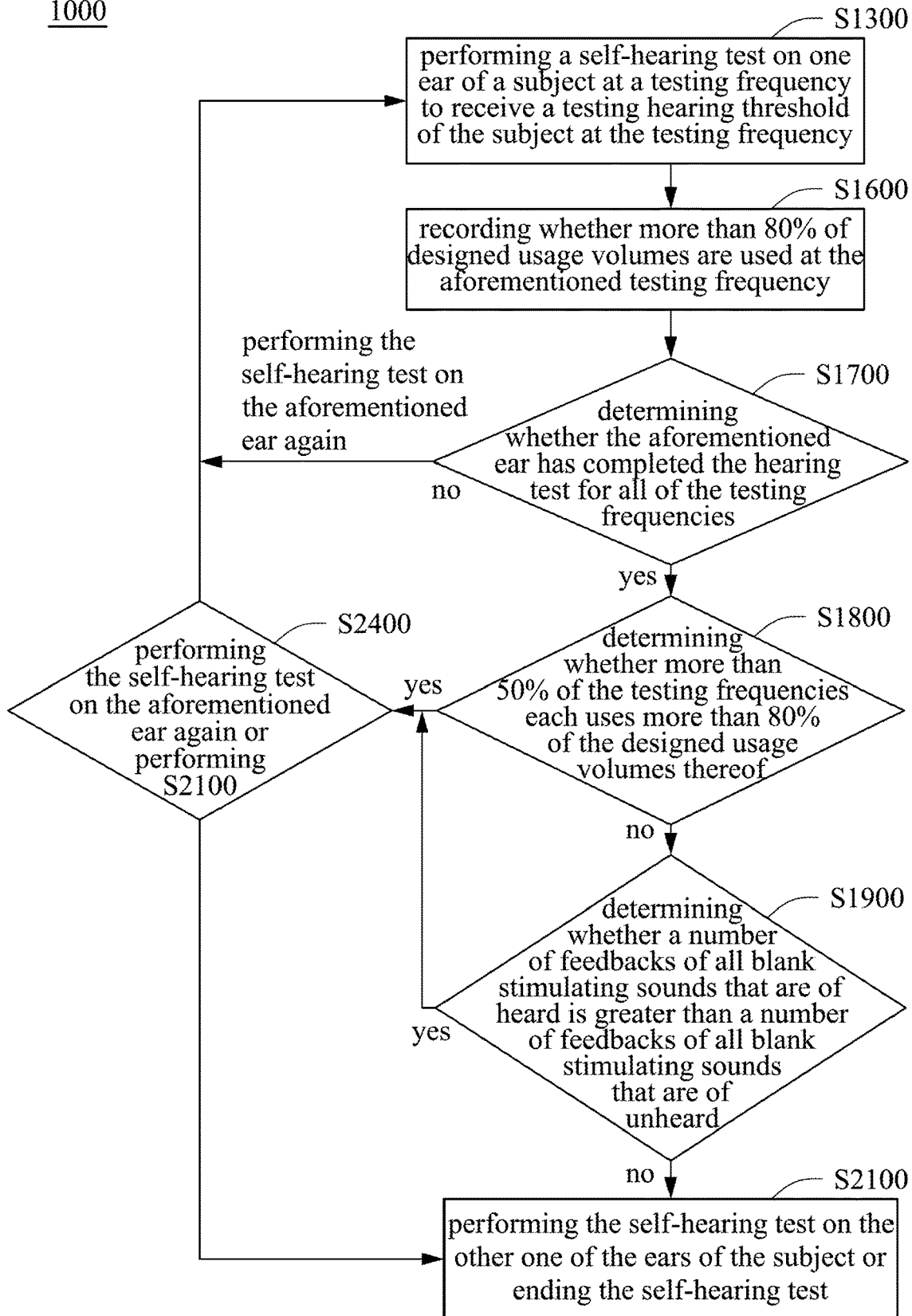
FIG. 2 illustrates a flowchart of a method for a hearing test according to some embodiments of the present disclosure.

Reference is made to FIG. 2. FIG. 2 illustrates a flowchart of method 1000 for a hearing test according to some embodiments of the present disclosure. It is understood that method 1000 shown in FIG. 2 has been simplified for a better understanding of the embodiments of the present disclosure. Accordingly, additional processes may be provided before, during, and after the stages of method 1000 shown in FIG. 2, and some other processes may be briefly described herein.

Specifically, method 1000 for the hearing test includes step S1300 to step S2400. In the embodiment, method 1000 for the hearing test is performed by using the hearing test system 1 as shown in FIG. 1 as an example.

Method 1000 for the hearing test begins at step S1300. In step S1300, with reference to FIGS. 3A-3H, a self-hearing test is performed on one ear of a subject at a testing frequency F1 to receive a testing hearing threshold of the subject at the testing frequency. In the embodiment, the testing frequency F1 is about 500 Hz, but the present disclosure is not limited thereto.

Specifically, according to an instruction of the control unit 36 of the electronic device 3, the sound generating unit 22 of the assistive listening device 2A is configured to generate a first testing sound at the testing frequency F1 for the aforementioned ear of the subject. Then, the subject conducts a feedback that is of heard or unheard on the user interface 34 of the electronic device 3 depending on whether the aforementioned ear may be able to hear the first testing sound. For example, if the subject conducts a feedback that is of heard on the user interface 34 of the electronic device 3, then the subject may be able to hear the first testing sound. Relatively, if the subject conducts a feedback that is of unheard on the user interface 34 of the electronic device 3, then the subject may be not able to hear the first testing sound.

Then, if the control unit 36 of the electronic device 3 determines that a first feedback received by the user interface 34 is of heard, then the control unit 36 may be configured to drive the sound generating unit 22 of the assistive listening device 2A selectively to generate a second testing sound that a volume thereof is less than or substantially equal to the volume of the first testing sound based on the lower testing limit TL at the testing frequency F1, and then determines the first testing hearing threshold of the subject at the testing frequency F1.

Relatively, if the control unit 36 of the electronic device 3 determines that the first feedback received by the user interface 34 is of unheard, then the control unit 36 may be configured to drive the sound generating unit 22 of the assistive listening device 2A selectively to generate a third testing sound that a volume thereof is greater than or substantially equal to the volume of the first testing sound based on the upper testing limit TH at the testing frequency F1, and then determines the first testing hearing threshold of the subject at the testing frequency F1.

For example, reference is made to FIGS. 3A-3H. FIGS. 3A-3H illustrate diagrams of feedback status of different subjects A, B, C, D, E, F, G, and H respectively, for some volumes substantially at the same frequency (e.g., 500 Hz) according to some embodiments of the present disclosure.

Figure 3B:
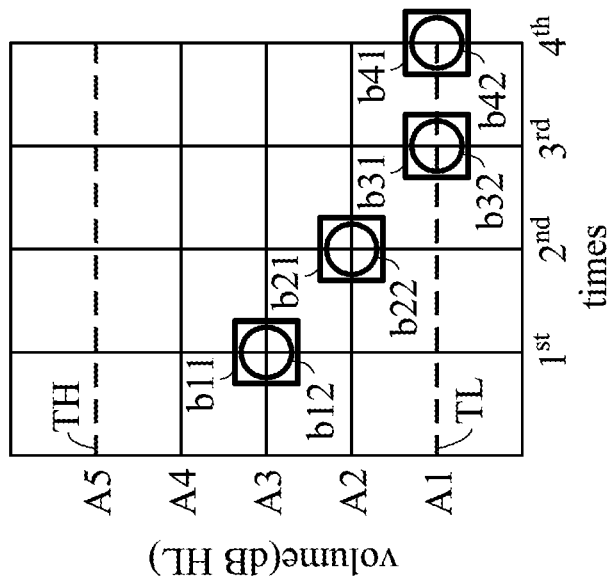
FIGS. 3A-3H illustrate diagrams of feedback status of different subjects, respectively, for some volumes substantially at the same frequency according to some embodiments of the present disclosure.
Figure 3A:
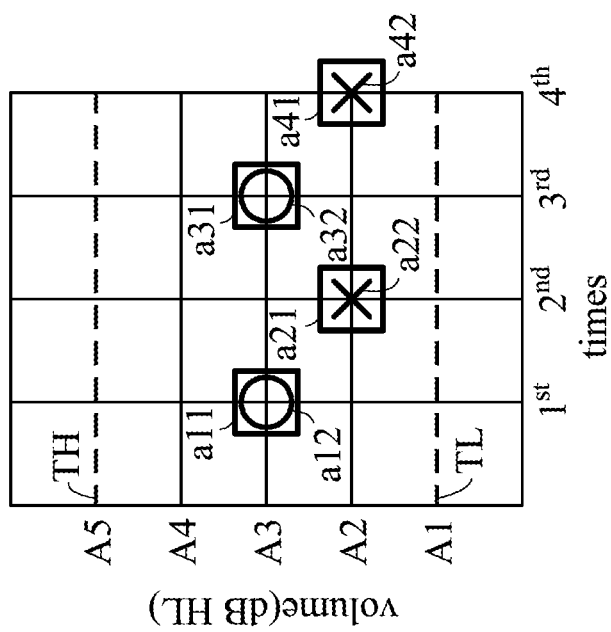

In FIG. 3A, according to an instruction of the control unit 36 of the electronic device 3, the sound generating unit 22 of the assistive listening device 2A is configured to generate a testing sound a11 at the testing frequency F1 for the aforementioned ear of the subject A. For example, the volume of the testing sound a11 may be about the volume A3, but the present disclosure is not limited thereto. Then, the aforementioned ear of the subject A may be able to hear the testing sound a11, and the subject A conducts a feedback a12 that is of heard on the user interface 34 of the electronic device 3.

Then, the control unit 36 of the electronic device 3 is configured to determine that the feedback a12 received by the user interface 34 is of heard, and further determine that the volume of the testing sound a11 does not equal to the lower testing limit TL, thereby driving the sound generating unit 22 of the assistive listening device 2A to generate a testing sound a21 that a volume thereof is less than the volume of the testing sound a11 for the subject A. For example, the volume of the testing sound a21 may be about the volume A2, but the present disclosure is not limited thereto.

Then, the aforementioned ear of the subject A may not be able to hear the testing sound a21, and thus the subject A conducts a feedback a22 that is of unheard on the user interface 34 of the electronic device 3. The control unit 36 of the electronic device 3 is configured to determine that the feedback a22 received by the user interface 34 is of unheard, and further determine that the volume of the testing sound a21 does not equal to the upper testing limit TH, thereby driving the sound generating unit 22 of the assistive listening device 2A to generate a testing sound a31 that a volume thereof is greater than the volume of the testing sound a21 for the subject A. For example, a volume of the testing sound a31 may be about the volume A3, but the present disclosure is not limited thereto.

Then, the aforementioned ear of the subject A may be able to hear the testing sound a31, and thus the subject A conducts a feedback a32 that is of heard on the user interface 34 of the electronic device 3. The control unit 36 of the electronic device 3 is configured to determine that the feedback a32 that is of heard received by the user interface 34, and further determine that the volume of the testing sound a31 does not equal to the lower testing limit TL, thereby driving the sound generating unit 22 of the assistive listening device 2A to generate a testing sound a41 that a volume thereof is less than the volume of the testing sound a31 for the subject A. For example, the volume of the testing sound a41 may be about the volume A2, but the present disclosure is not limited thereto. Then, the aforementioned ear of the subject A may not be able to hear the testing sound a41, and thus the subject A conducts a feedback a42 that is of unheard on the user interface 34 of the electronic device 3.

At this time, when the control unit 36 of the electronic device 3 is configured to determine that a number of the testing sounds generated by the sound generating unit 22 is at least four times and the feedbacks a12, a22, a32, and a42 based on the last four testing sounds are sequentially of heard, unheard, heard, and unheard, the control unit 36 of the electronic device 3 is configured to stop the sound generating unit 22 of the assistive listening device 2A from generating the sound at the testing frequency F1. Therefore, the aforementioned ear ends the self-hearing test at the testing frequency F1, and obtains the testing hearing threshold of the subject A that may be about the volume A3 at the testing frequency F1.

In FIG. 3B, according to an instruction of the control unit 36 of the electronic device 3, the sound generating unit 22 of the assistive listening device 2A is configured to generate a testing sound b11 at the testing frequency F1 for the subject B. In the embodiment, testing sounds b11 and b21 and a feedback b12 are substantially the same as the testing sounds a11 and a21 and the feedback a12 shown in FIG. 3A, respectively, and the related detailed descriptions may refer to the foregoing paragraphs, and are not described again herein.

It is noted that, the difference between the present embodiment and the embodiment in FIG. 3A is in that an ear of the subject B may be able to hear the testing sound b21, and thus the subject B conducts a feedback b22 that is of heard on the user interface 34 of the electronic device 3. The control unit 36 of the electronic device 3 is configured to determine that the feedback b22 received by the user interface 34 is of heard, and further determine that a volume of the testing sound b21 does not equal to the lower testing limit TL, thereby driving the sound generating unit 22 of the assistive listening device 2A to generate a testing sound b31 that a volume thereof is less than the volume of the testing sound b21 for the subject B. For example, the volume of the testing sound b31 may be about the volume A1, but the present disclosure is not limited thereto.

Then, the ear of the subject B may be able to hear the testing sound b31, and thus the subject B conducts a feedback b32 that is of heard on the user interface 34 of the electronic device 3. The control unit 36 of the electronic device 3 is configured to determine that the feedback b32 received by the user interface 34 is of heard, and further determine that the volume of the testing sound b31 substantially equals to the lower testing limit TL, thereby driving the sound generating unit 22 of the assistive listening device 2A to generate a testing sound b41 that a volume thereof substantially equals to the volume of the testing sound b31 for the subject B. Then, the ear of the subject B may be able to hear the testing sound b41, and thus the subject B conducts the feedback b42 that is of heard on the user interface 34 of the electronic device 3.

At this time, when the control unit 36 of the electronic device 3 is configured to determine that the testing sounds generated by the sound generating unit 22 have a number that is at least twice, volumes thereof substantially both equal to the lower testing limit TL, and the feedback b32 and b42 thereof both are of heard, the control unit 36 of the electronic device 3 is configured to stop the sound generating unit 22 of the assistive listening device 2A from generating the sound at the testing frequency F1. Therefore, the aforementioned ear ends the self-hearing test at the testing frequency F1, and obtains the testing hearing threshold of the subject B that may be about the volume A1 at the testing frequency F1.

Figure 3D:
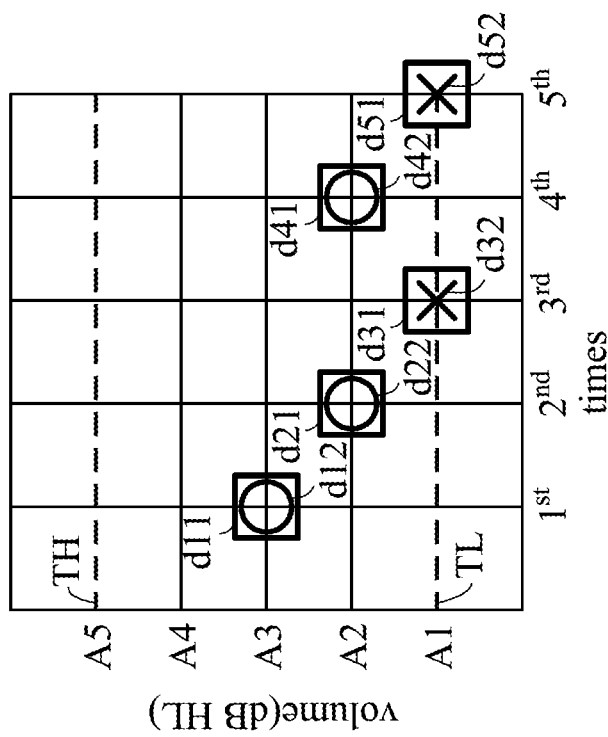
Figure 3C:
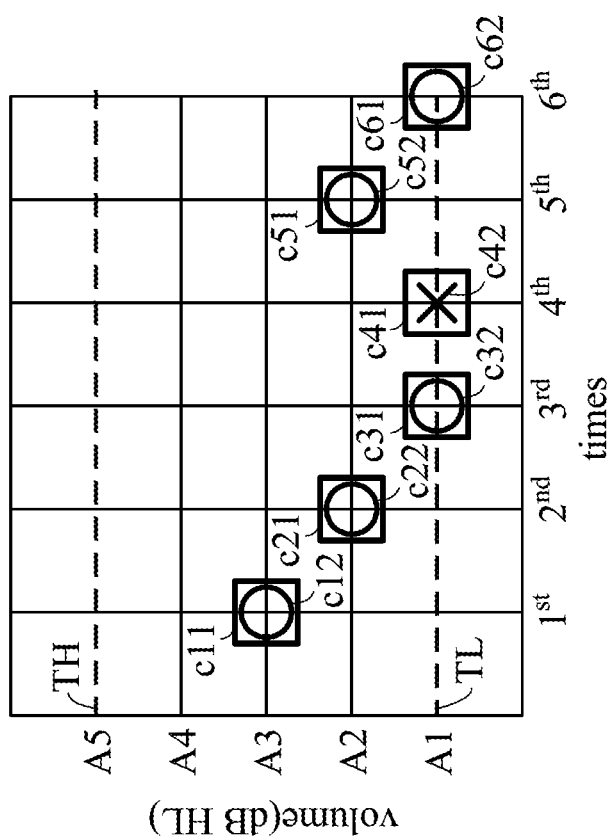

In FIG. 3C, according to an instruction of the control unit 36 of the electronic device 3, the sound generating unit 22 of the assistive listening device 2A is configured to generate a testing sound c11 at the testing frequency F1 for the subject C. In the embodiment, testing sounds c11, c21, c31, and c41 and feedback c12, c22, and c32 are substantially the same as the testing sounds b11, b21, b31, and b41 and the feedbacks b12, b22, and b32 shown in FIG. 3B, respectively, and the related detailed descriptions may refer to the foregoing paragraphs, and are not described again herein.

It is noted that, the difference between the present embodiment and the embodiment in FIG. 3B is in that the subject C may be not able to hear the testing sound b41, and thus the subject C conducts a feedback c42 that is of unheard on the user interface 34 of the electronic device 3. The control unit 36 of the electronic device 3 is configured to determine that the feedback c42 received by the user interface 34 is of unheard, and further determine that a volume of the testing sound c41 substantially equals to the lower testing limit TL, thereby driving the sound generating unit 22 of the assistive listening device 2A to generate a testing sound c51 that a volume thereof is greater than the volume of the testing sound c41 for the subject C. For example, the volume of the testing sound c51 may be about the volume A2, but the present disclosure is not limited thereto.

Then, the ear of the subject C may be able to hear the testing sound c51, and thus the subject C conducts a feedback c52 that is of heard on the user interface 34 of the electronic device 3. The control unit 36 of the electronic device 3 is configured to determine that the feedback c52 received by the user interface 34 is of heard, and further determine that the volume of the testing sound c51 does not equal to the lower testing limit TL, thereby driving the sound generating unit 22 of the assistive listening device 2A to generate a testing sound c61 that a volume thereof is less than the volume of the testing sound c51 for the subject C. Then, the ear of the subject C may be able to hear the testing sound c61, and thus the subject C conducts a feedback c62 that is of heard on the user interface 34 of the electronic device 3.

At this time, when the control unit 36 of the electronic device 3 is configured to determine that the testing sounds generated by the sound generating unit 22 have a number that is at least twice, volumes thereof substantially both equal to the lower testing limit TL, and the feedback c32 and c62 thereof both are of heard, the control unit 36 of the electronic device 3 is configured to stop the sound generating unit 22 from generating the sound at the testing frequency F1. Therefore, the aforementioned ear ends the self-hearing test at the testing frequency F1, and obtains the testing hearing threshold of the subject C that may be about the volume A1 at the testing frequency F1.

In FIG. 3D, according to an instruction of the control unit 36 of the electronic device 3, the sound generating unit 22 of the assistive listening device 2A is configured to generate a testing sound d11 at the testing frequency F1 for the subject D. In the embodiment, testing sounds d11, d21, and d31 and feedbacks d12 and d22 are substantially the same as the testing sound b11, b21, and b31 and the feedbacks b12 and b22 shown in FIG. 3B, respectively, and the related detailed descriptions may refer to the foregoing paragraphs, and are not described again herein.

It is noted that, the difference between the present embodiment and the embodiment in FIG. 3B is in that an ear of the subject D may be not able to hear the testing sound d31, and thus the subject D conducts a feedback d32 that is of unheard on the user interface 34 of the electronic device 3. The control unit 36 of the electronic device 3 is configured to determine that a feedback d32 received by the user interface 34 is of unheard, and further determine that a volume of the testing sound d31 substantially equals to the lower testing limit TL, thereby driving the sound generating unit 22 of the assistive listening device 2A to generate a testing sound d41 that a volume thereof is greater than the volume of the testing sound d31 for the subject D. For example, the volume of the testing sound d41 may be about the volume A2, but the present disclosure is not limited thereto.

Then, the ear of the subject D may be able to hear the testing sound d41, and thus the subject D conducts a feedback d42 that is of heard on the user interface 34 of the electronic device 3. The control unit 36 of the electronic device 3 is configured to determine that the feedback d42 received by the user interface 34 is of heard, and further determine that the volume of the testing sound d41 does not equal to the lower testing limit TL, thereby driving the sound generating unit 22 of the assistive listening device 2A to generate a testing sound d51 that a volume thereof is less than the volume of the testing sound d41 for the subject D. Then, the ear of the subject D may be not able to hear a testing sound d51, and the subject D conducts a feedback d52 that is of unheard on the user interface 34 of the electronic device 3.

At this time, when the control unit 36 of the electronic device 3 is configured to determine that the testing sounds generated by the sound generating unit 22 have a number that is at least twice, volumes thereof substantially both equal to the lower testing limit TL, and the feedbacks d32 and d52 thereof both are of unheard, and that the two testing sounds with the volumes A2 have the feedbacks d22 and d42 that both are of heard, the control unit 36 of the electronic device 3 is configured to stop the sound generating unit 22 from generating the sound at the testing frequency F1. Therefore, the aforementioned ear ends the self-hearing test at the testing frequency F1, and obtains the testing hearing threshold of the subject D that may be about the volume A2 at the testing frequency F1.

Figure 3F:
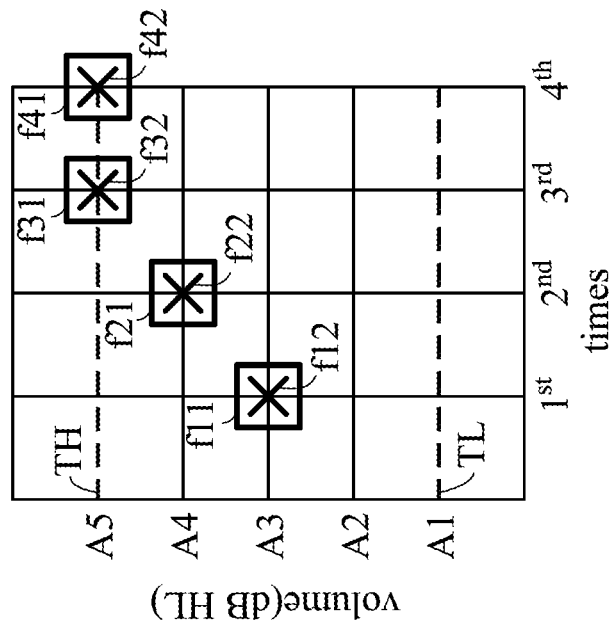
Figure 3E:
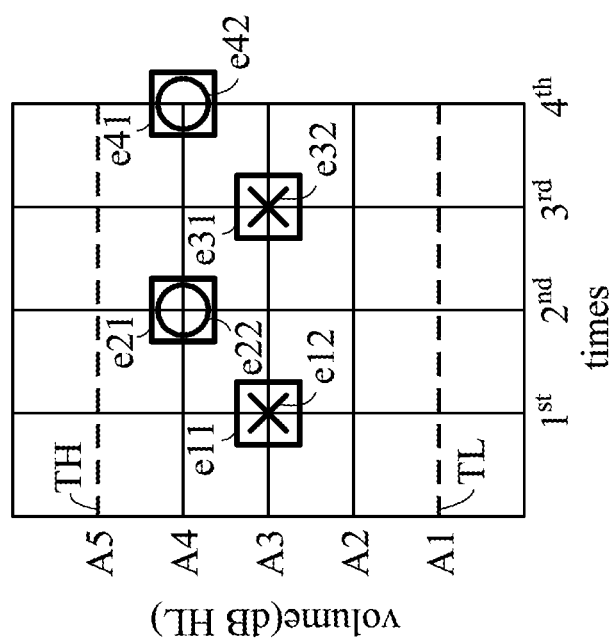

In FIG. 3E, according to an instruction of the control unit 36 of the electronic device 3, the sound generating unit 22 of the assistive listening device 2A is configured to generate a testing sound e11 at the testing frequency F1 for the subject E. For example, a volume of the testing sound e11 may be about 50 dB, but the present disclosure is not limited thereto. Then, the ear of the subject E may be not able to hear the testing sound e11, and thus the subject E conducts a feedback e12 that is of unheard on the user interface 34 of the electronic device 3.

Then, the control unit 36 of the electronic device 3 is configured to determine that a feedback e12 received by the user interface 34 is of unheard, and further determine that whether the volume of the testing sound e11 does not equal to the upper testing limit TH, thereby driving the sound generating unit 22 of the assistive listening device 2A to generate a testing sound e21 that a volume thereof is greater than the volume of the testing sound e11 for the subject E. For example, the volume of the testing sound e21 may be about the volume A4, but the present disclosure is not limited thereto.

Then, the ear of the subject E may be able to hear the testing sound e21, and thus the subject E conducts a feedback e22 that is of heard on the user interface 34 of the electronic device 3. The control unit 36 of the electronic device 3 is configured to determine that the feedback e22 received by the user interface 34 is of heard, and further determine that the volume of the testing sound e21 does not equal to the lower testing limit TL, thereby driving the sound generating unit 22 of the assistive listening device 2A to generate a testing sound e31 that a volume thereof is less than the volume of the testing sound e21 for the subject E. For example, a volume of the testing sound e31 may be about the volume A3, but the present disclosure is not limited thereto.

Then, the ear of the subject E may be not able to hear the testing sound e31, and thus the subject E conducts a feedback e32 that is of unheard on the user interface 34 of the electronic device 3. The control unit 36 of the electronic device 3 is configured to determine that a feedback e32 received by the user interface 34 is of unheard, and further determine that a volume of the testing sound e31 does not equal to the upper testing limit TH, thereby driving the sound generating unit 22 of the assistive listening device 2A to generate a testing sound e41 that a volume thereof is greater than the volume of the testing sound e31 for the subject E. For example, the volume of the testing sound e41 may be about the volume A4, but the present disclosure is not limited thereto. Then, the ear of the subject E may be able to hear the testing sound e41, and thus the subject E conducts a feedback e42 that is of heard on the user interface 34 of the electronic device 3.

At this time, when the control unit 36 of the electronic device 3 is configured to determine a number of the testing sounds generated by the sound generating unit 22 is at least four times and the feedbacks e12, e22, e32, and e42 based on the last four testing sounds are sequentially of unheard, heard, unheard, and heard, the control unit 36 of the electronic device 3 is configured to stop the sound generating unit 22 from generating the sound at the testing frequency F1. Therefore, the aforementioned ear ends the self-hearing test at the testing frequency F11, and obtains the testing hearing threshold of the subject E that may be about the volume A4 at the testing frequency F1.

In FIG. 3F, according to an instruction of the control unit 36 of the electronic device 3, the sound generating unit 22 of the assistive listening device 2A is configured to generate a testing sound f11 at the testing frequency F1 for the subject F. In the embodiment, testing sounds f11 and f21 and a feedback f12 are substantially the same as the testing sounds e11 and e21 and the feedback e12 shown in FIG. 3E, respectively, and the related detailed descriptions may refer to the foregoing paragraphs, and are not described again herein.

It is noted that, the difference between the present embodiment and the embodiment in FIG. 3E is in that the ear of the subject F may be not able to hear the testing sound f21, and thus the subject F conducts a feedback f22 that is of unheard on the user interface 34 of the electronic device 3. The control unit 36 of the electronic device 3 is configured to determine that a feedback f22 received by the user interface 34 is of unheard, and further determine that a volume of the testing sound f21 does not equal to the upper testing limit TH, thereby driving the sound generating unit 22 to generate a testing sound f31 that a volume thereof is greater than the volume of the testing sound f21 for the subject F. For example, the volume of the testing sound f31 may be about the volume A5, but the present disclosure is not limited thereto.

Then, the ear of the subject F may not be able to hear the testing sound f31, and thus the subject F conducts a feedback f32 that is of unheard on the user interface 34 of the electronic device 3. The control unit 36 of the electronic device 3 is configured to determine that the feedback f32 received by the user interface 34 is of unheard, and further determine that the volume of the testing sound f31 substantially equals to the upper testing limit TH, thereby driving the sound generating unit 22 of the assistive listening device 2A to generate a testing sound f41 that a volume thereof substantially equals to the volume of the testing sound f31 for the subject F. Then, the ear of the subject F may not be able to hear the testing sound f41, and thus the subject F conducts the feedback f42 that is of unheard on the user interface 34 of the electronic device 3.

At this time, when the control unit 36 of the electronic device 3 is configured to determine that the testing sounds generated by the sound generating unit 22 have a number that is at least twice, volumes thereof substantially both equal to the upper testing limit TH, and the feedbacks f32 and f42 thereof both are of unheard, the control unit 36 of the electronic device 3 is configured to stop the sound generating unit 22 from generating the sound at the testing frequency F1. Therefore, the aforementioned ear ends the self-hearing test at the testing frequency F1, and obtains the testing hearing threshold of the subject F that may be at least greater than the volume A5 at the testing frequency F1.

Figure 3H:
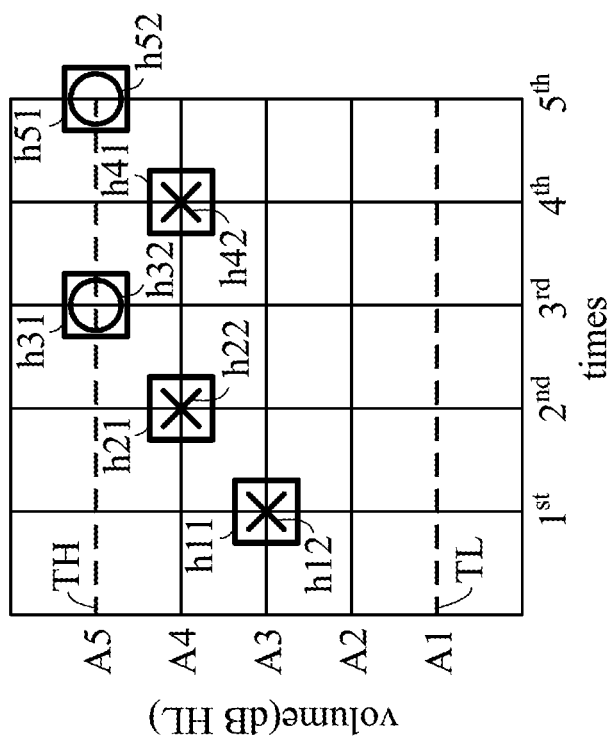
Figure 3G:
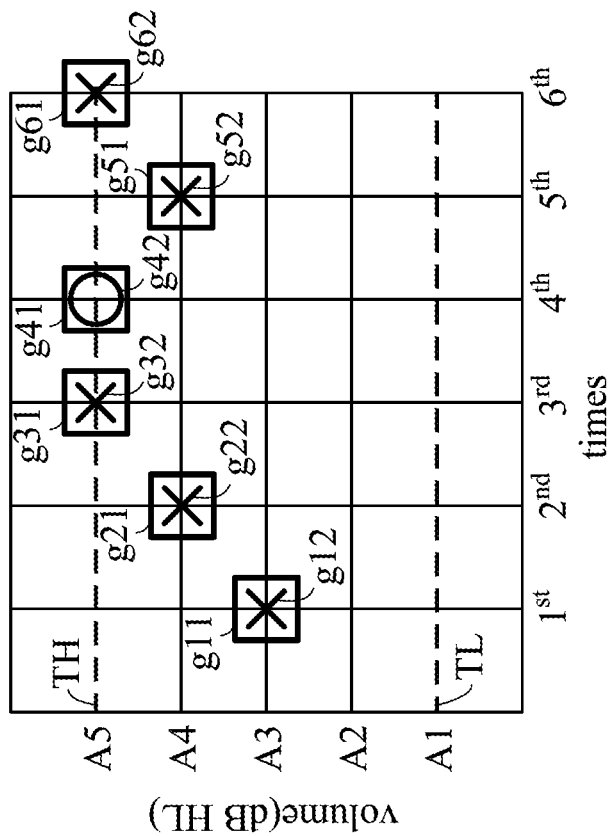

In FIG. 3G, according to an instruction of the control unit 36 of the electronic device 3, the sound generating unit 22 of the assistive listening device 2A is configured to generate a testing sound g11 at the testing frequency F1 for the subject G. In the embodiment, testing sounds g11, g21, g31, and g41 and feedbacks g12, g22, and g32 are substantially the same as the testing sounds f11, f21, f31, and f41 and the feedbacks f12, f22, and f32 shown in FIG. 3F, respectively, and the related detailed descriptions may refer to the foregoing paragraphs, and are not described again herein.

It is noted that, the difference between the present embodiment and the embodiment in FIG. 3F is in that the ear of the subject G may be able to hear a testing sound g41, and thus the subject G conducts a feedback g42 that is of heard on the user interface 34 of the electronic device 3. The control unit 36 of the electronic device 3 is configured to determine that the feedback g42 received by the user interface 34 is of heard, and further determine that a volume of the testing sound g41 substantially equals to sthe upper testing limit TH, thereby driving the sound generating unit 22 to generate a testing sound g51 that a volume thereof is less than the volume of the testing sound g41 for the subject G. For example, a volume of the testing sound g51 may be about the volume A4, but the present disclosure is not limited thereto.

Then, the ear of the subject G may not be able to hear the testing sound g51, and thus the subject G conducts a feedback g52 that is of unheard on the user interface 34 of the electronic device 3. The control unit 36 of the electronic device 3 is configured to determine that the feedback g52 received by the user interface 34 is of unheard, and further determine that the volume of the testing sound g51 not equals to the upper testing limit TH, thereby driving the sound generating unit 22 of the assistive listening device 2A to generate a testing sound g61 that a volume thereof is greater than the volume of the testing sound g51 for the subject G. Then, the ear of the subject G may not be able to hear the testing sound the testing sound g61, and thus the subject G conducts a feedback g62 that is of unheard on the user interface 34 of the electronic device 3.

At this time, when the control unit 36 of the electronic device 3 is configured to determine that the testing sounds generated by the sound generating unit 22 have a number that is at least twice, volumes thereof substantially both equal to the upper testing limit TH, and the feedbacks g32 and g62 thereof both are of unheard, the control unit 36 of the electronic device 3 is configured to stop the sound generating unit 22 from generating the sound at the testing frequency F1. Therefore, the aforementioned ear ends at the self-hearing test at the testing frequency F1, and obtains the testing hearing threshold of the subject G may be at least greater than the volume A5 at the testing frequency F1.

In FIG. 3H, according to an instruction of the control unit 36 of the electronic device 3, the sound generating unit 22 of the assistive listening device 2A is configured to generate a testing sound h11 at the testing frequency F1 for the subject H. In the embodiment, testing sounds h11, h21, and h31 and feedbacks h12 and h22 are substantially the same as the testing sounds f11, f21, and f31 and the feedbacks f12 and f22 shown in FIG. 3F, respectively, and the related detailed descriptions may refer to the foregoing paragraphs, and are not described again herein.

It is noted that, the difference between the present embodiment and the embodiment in FIG. 3F is in that the ear of the subject H may be able to hear a testing sound h31, and thus the subject H conducts a feedback h32 that is of heard on the user interface 34 of the electronic device 3. The control unit 36 of the electronic device 3 is configured to determine that the feedback h32 received by the user interface 34 is of heard, and further determine that a volume of the testing sound h31 substantially equals to the upper testing limit TH, thereby driving the sound generating unit 22 to generate a testing sound h41 that a volume thereof is less than the volume of the testing sound h31 for the subject H. For example, the volume of the testing sound h41 may be about the volume A4, but the present disclosure is not limited thereto.

Then, the ear of the subject H may not be able to hear the testing sound h41, and thus the subject H conducts a feedback h42 that is of unheard on the user interface 34 of the electronic device 3. The control unit 36 of the electronic device 3 is configured to determine that the feedback h42 received by the user interface 34 is of unheard, and further determine that a volume of the testing sound h41 does not equal to the upper testing limit TH, thereby driving the sound generating unit 22 of the assistive listening device 2A to generate a testing sound h51 that a volume thereof is greater than the volume of the testing sound h41 for the subject H. Then, the ear of the subject H may be able to hear the testing sound h51, and thus the subject H conducts a feedback h52 that is of heard on the user interface 34 of the electronic device 3.

At this time, when the control unit 36 of the electronic device 3 is configured to determine that the testing sounds generated by the sound generating unit 22 have a number that is at least twice, volumes thereof substantially both equal to the upper testing limit TH, and the feedback h32 and h52 of the testing sounds h31 and h51 both are of heard, the control unit 36 of the electronic device 3 is configured to stop the sound generating unit 22 from generating the sound at the testing frequency F1. Therefore, the aforementioned ear ends at the self-hearing test at the testing frequency F1, and obtains the testing hearing threshold of the subject H that may be about the volume A5 at the testing frequency F1.

Figure 4:
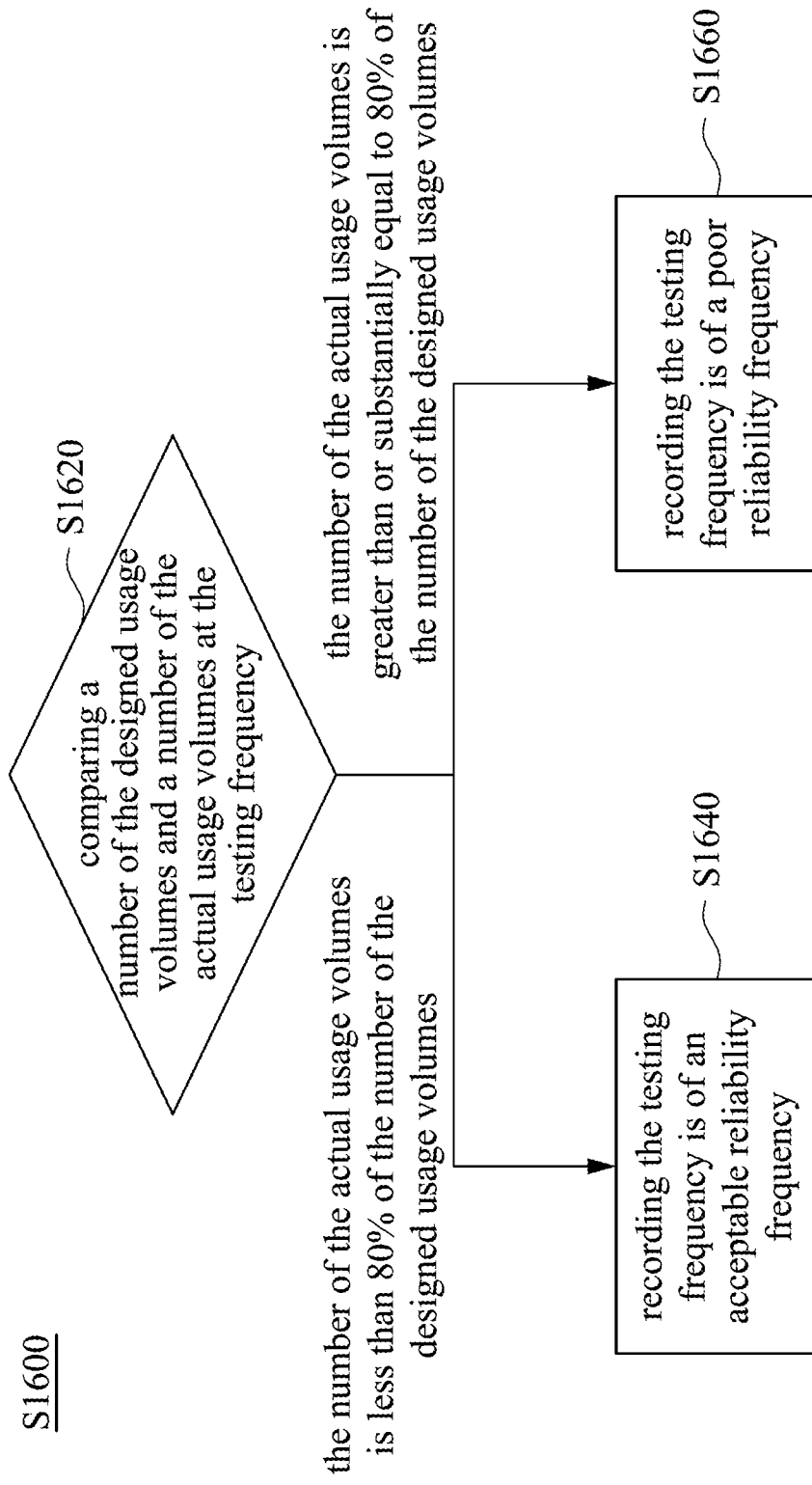
FIG. 4 illustrates a flowchart for determining the credibility of a hearing test according to some embodiments of the present disclosure.

Reference is made to FIG. 2. Method 1000 for the hearing test then proceeds to step S1600. In step S1600, the storage unit 30 of the electronic device 3 records whether more than 80% of the designed usage volumes are used at the aforementioned testing frequency. Specifically, reference is made to FIG. 4. FIG. 4 illustrates a flowchart for determining the credibility of a hearing test according to some embodiments of the present disclosure.

It is understood that step S1600 shown in FIG. 4 has been simplified for a better understanding of the embodiments of the present disclosure. Accordingly, additional processes may be provided before, during, and after the stages of step S1600 shown in FIG. 4, and some other processes may be briefly described herein. Specifically, step S1600 further includes step S1620 to step S1660.

In step S1620, the control unit 36 of the electronic device 3 is configured to calculate a number of designed usage volumes for a testing frequency, to calculate a number of actual usage volumes of the aforementioned testing frequency after the hearing test, and further to compare the number of the designed usage volumes and the number of the actual usage volumes. When the number of the actual usage volumes is less than 80% of the number of the designed usage volumes, Method 1000 for the hearing test then proceeds to step S1640 and the aforementioned testing frequency is summarized as an acceptable reliability frequency. When the number of the actual usage volumes is greater than or substantially equal to 80% of the number of the designed usage volumes, Method 1000 for the hearing test then proceeds to step S1660 and the aforementioned testing frequency is summarized as a poor reliability frequency. In step S1640, the storage unit 30 of the electronic device 3 records the testing frequency that is of the acceptable reliability frequency. In step S1660, the storage unit 30 of the electronic device 3 records the testing frequency that is of the poor reliability frequency.

For example, in FIG. 3A, the control unit 36 of the electronic device 3 is configured to calculate a number of designed usage volumes that is five for the testing frequency F1 and a number of actual usage volumes that is two for the testing frequency F1. The number of actual usage volumes is 40% of the number of designed usage volumes, which is less than 80% of the number of designed usage volumes, and thus Method 1000 for the hearing test may then proceed to step S1640 and the testing frequency F1 is summarized as the acceptable reliability frequency. In step S1640, the storage unit 30 of the electronic device 3 records the testing frequency F1 that is of the acceptable reliability frequency.

Reference is made to FIG. 2. Method 1000 for the hearing test then proceeds to step S1700. In step S1700, the control unit 36 of the electronic device 3 is configured to determine whether the aforementioned ear has completed the hearing test for all of the testing frequencies. When the aforementioned ear has completed the hearing test for each of all of the testing frequencies, Method 1000 for the hearing test may then proceed to step S1800. When the aforementioned ear is not completed the hearing test for each of all of the testing frequencies, Method 1000 for the hearing test may then proceed to step S1300 and step S1600 for the other untested testing frequencies, respectively.

Figure 5A:
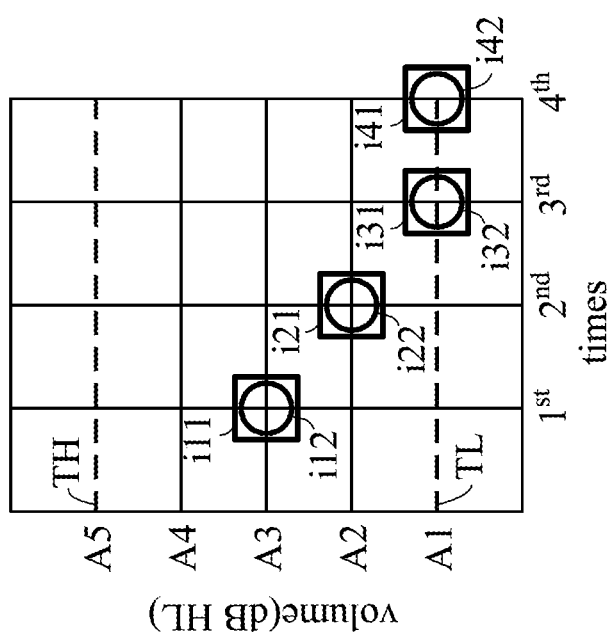
FIGS. 5A-5C illustrate diagrams of feedback status of the same subject for some volumes at different frequencies, respectively, according to some embodiments of the present disclosure.
Figure 5C:
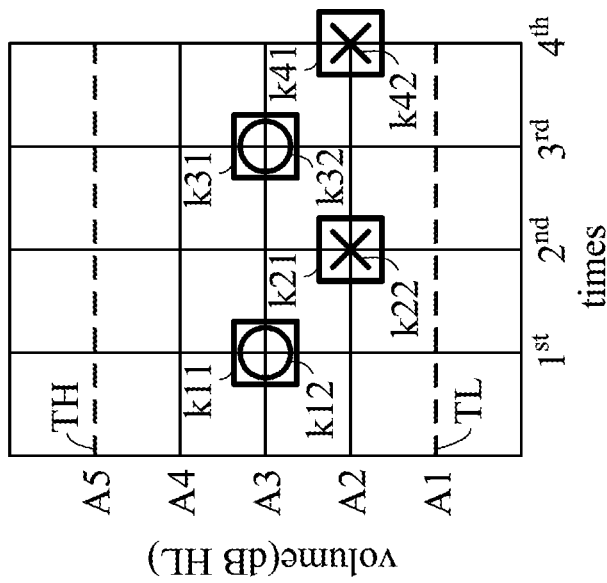
Figure 5C:
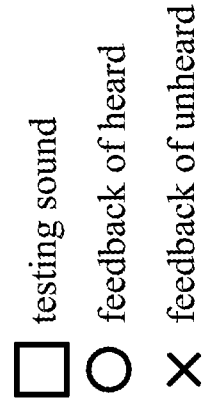
Figure 5B:
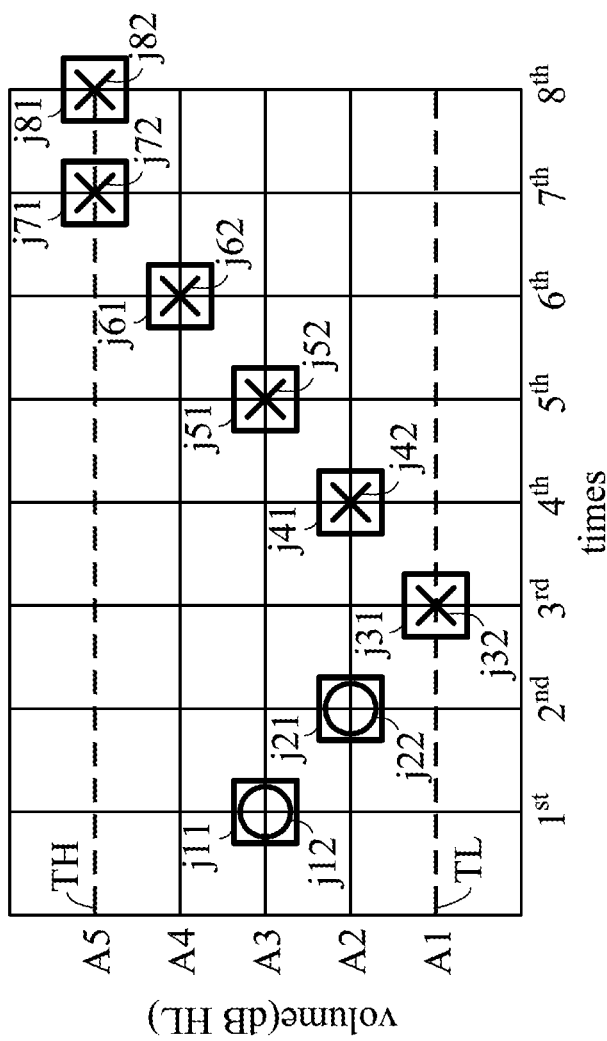

In the embodiment, method 1000 for the hearing test is also designed to perform the self-hearing test on the aforementioned ear of the subject A at different testing frequencies F2, F3, and F4. For example, the testing frequencies F2, F3, and F4 may be about 1 kHz, about 2 kHz, and about 4 kHz, respectively, but the present disclosure is not limited thereto. In some embodiments, the value and quantity of the testing frequency can be designed according to actual needs. Reference is made to FIGS. 5A-5C. FIGS. 5A-5C illustrate diagrams of feedback status of the same subject A for some volumes at different frequencies F2, F3, and F4, respectively, according to some embodiments of the present disclosure.

In FIG. 5A, the control unit 36 of the electronic device 3 is configured to calculate a number of designed usage volumes that is five for the testing frequency F2 and a number of actual usage volumes that is three for the testing frequency F2. The number of actual usage volumes is 60% of the number of designed usage volumes, which is less than 80% of the number of designed usage volumes, and thus Method 1000 for the hearing test may then proceed to step S1640 and the testing frequency F2 is summarized as the acceptable reliability frequency. In step S1640, the storage unit 30 of the electronic device 3 records the testing frequency F2 is of the acceptable reliability frequency.

In FIG. 5B, the control unit 36 of the electronic device 3 is configured to calculate a number of designed usage volumes that is five for the testing frequency F3 and a number of actual usage volumes that is five for the testing frequency F3. The number of actual usage volumes is 100% of the number of designed usage volumes, which is higher than 80% of the number of designed usage volumes, and thus Method 1000 for the hearing test may then proceed to step S1660 and the testing frequency F3 is summarized as the poor reliability frequency. In step S1660, the storage unit 30 of the electronic device 3 records the testing frequency F3 is of the poor reliability frequency.

In FIG. 5C, the control unit 36 of the electronic device 3 is configured to calculate a number of designed usage volumes that is five for the testing frequency F4 and a number of actual usage volumes that is two for the testing frequency F4. The number of actual usage volumes is 40% of the number of designed usage volumes, which is less than 80% of the number of designed usage volumes, and thus Method 1000 for the hearing test may then proceed to step S1640 and the testing frequency F4 is summarized as the acceptable reliability frequency. In step S1640, the storage unit 30 of the electronic device 3 records the testing frequency F4 is of the acceptable reliability frequency. Specifically, Table. 1 shows the result of the self-hearing test performed by one of the ears of the subject A at the different testing frequencies, as shown below.

TABLE 1 the result of the self-hearing test performed by one of the ears of the subject A at the different testing frequencies

| testing frequency (Hz) | number of designed usage volumes (N1) | second number of actual usage volumes (N2) | N2/N1 | N2/N1 ≥ 80% (Y/N) | acceptable reliability frequency or poor reliability frequency |
|---|---|---|---|---|---|
| 500 | 5 | 2 | 40% | N | acceptable reliability frequency |
| 1000 | 5 | 3 | 60% | N | acceptable reliability frequency |
| 2000 | 5 | 5 | 100% | Y | poor reliability frequency |
| 4000 | 5 | 2 | 40% | N | acceptable reliability frequency |

Reference is made to FIG. 2. Method 1000 for the hearing test then proceeds to step S1800. In step S1800, the control unit 36 of the electronic device 3 is configured to determine whether more than 50% of the testing frequencies each uses more than 80% of the designed usage volumes thereof to further determine a reliability of the hearing test. When more than 50% of the testing frequencies each uses more than 80% of the designed usage volumes thereof, the aforementioned hearing test is set to be of a poor reliability and method 1000 may then proceed to step S2400. That is, when a number of the poor reliability frequency divided by a number of the testing frequencies is greater than or substantially equals to 50%, the hearing test is of the poor reliability and method 1000 may then proceed to step S2400.

Relatively, when more than 50% of the testing frequencies each does not use more than 80% of the designed usage volumes thereof, the aforementioned hearing test is set to be of an acceptable reliability and method 1000 may then proceed to step S1900. That is, when a number of the poor reliability frequency divided by a number of the testing frequencies is less than 50%, the hearing test is of the acceptable reliability and method 1000 may then proceed to step S1900.

For example, as shown in FIGS. 5A-5C and table. 1, a number of the poor reliability frequency is one and a number of the testing frequencies is four. The number of the poor reliability frequency divided by the number of the testing frequencies is 25%, which is less than 50%, and thus the hearing test is summarized as the acceptable reliability and method 1000 may then proceed to step S1900. Specifically, Table. 2 shows the result of the reliability of the self-hearing test of one of the ears of the subjects A, as shown below.

TABLE 2 the result of the reliability of the self-hearing test of one of the ears of the subjects A

| number of testing frequency (N3) | number of poor reliability frequency (N4) | N4/N3 | N4/N3 ≥ 50% (Y/N) | acceptable reliability or poor reliability |
|---|---|---|---|---|
| 4 | 1 | 25% | N | acceptable reliability |

Reference is made to FIG. 2. Method 1000 for the hearing test then proceeds to step S1900. In step S1900, the control unit 36 of the electronic device 3 is configured to determine whether a number of feedbacks of all blank stimulating sounds that are of heard is greater than a number of feedbacks of all blank stimulating sounds that are of unheard. In the embodiment, the blank stimulating sound indicated that sound is not generated at all at a testing frequency in a hearing test. In other words, the volume of the blank stimulating sound may substantially equals to zero.

Figure 6:
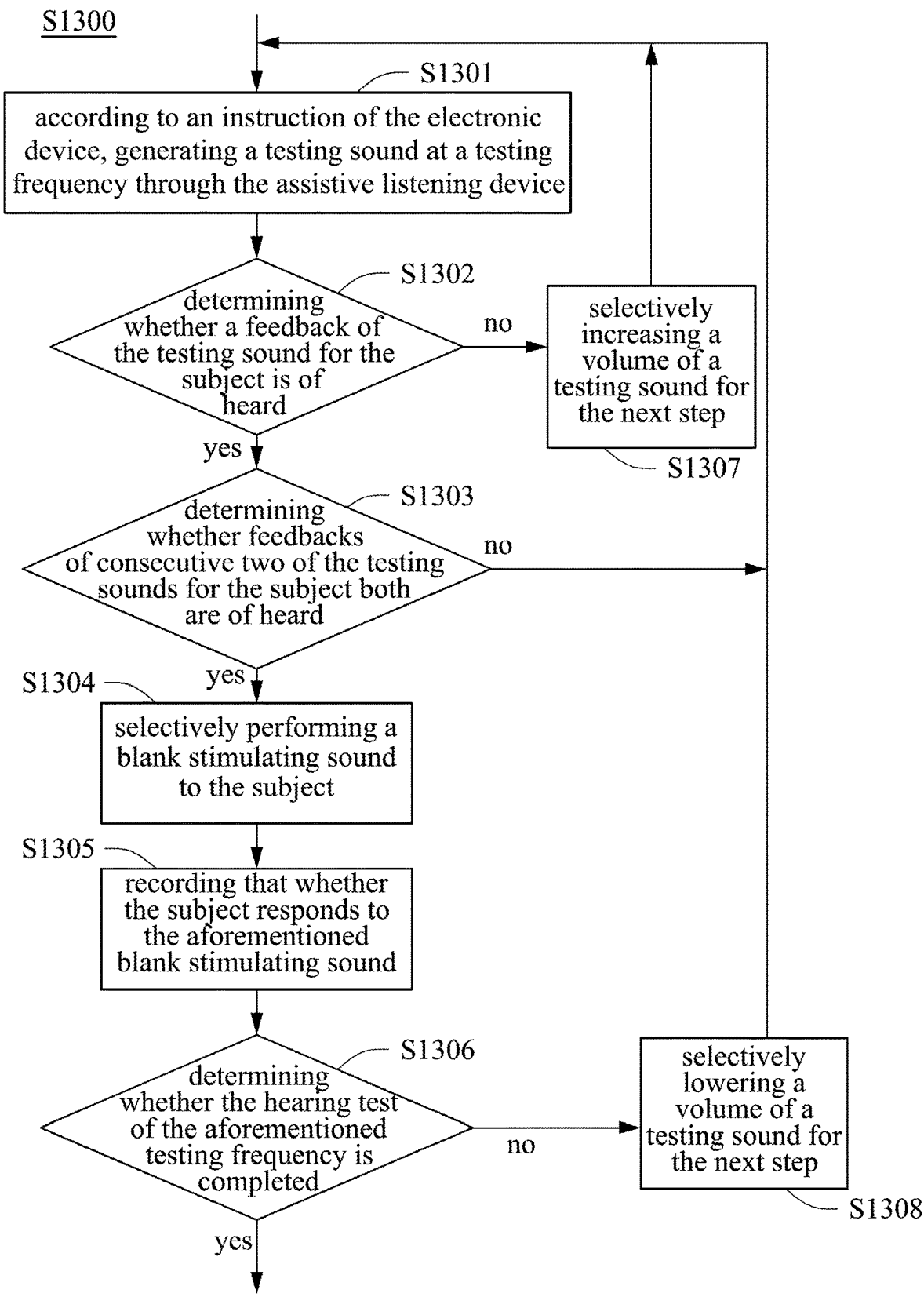
FIG. 6 illustrates a flowchart of a method for a hearing test according to some embodiments of the present disclosure.

In the embodiment, a credibility of method 1000 may be affected by the subject's improper operation of the hearing test system 1. Therefore, in step S1300 of method 1000 for the hearing test, a blank stimulating sound is inserted to verify the reliability of the data of method 1000 for the hearing test, thereby preventing the subject from adjusting a hearing function of the assistive listening device 2A by using the test result with poor reliability. As such, the accuracy of the assistive listening device 2A can be improved. Specifically, if the subject conducts a feedback of the blank stimulating sound that is of heard on the user interface 34 of the electronic device 3, it indicates that the subject may improperly operate the hearing test system 1. Relatively, if the subject conducts a feedback of the blank stimulating sound that is of unheard on the user interface 34 of the electronic device 3, then it indicates that the subject may correctly operate the hearing test system 1. Specifically, reference is made to FIG. 6. FIG. 6 illustrates a flowchart of step S1300 for a hearing test includes a blank stimulating sound according to some embodiments of the present disclosure.

It is understood that step S1300 shown in FIG. 6 has been simplified for a better understanding of the embodiments of the present disclosure. Accordingly, additional processes may be provided before, during, and after the stages of step S1300 shown in FIG. 6, and some other processes may be briefly described herein. Further, one or more of the steps depicted herein may be implemented in one or more separate steps and/or stages. Specifically, step S1300 of method 1000 for the hearing test further includes step S1301 to step S1308 as shown in FIG. 6.

Figure 7B:
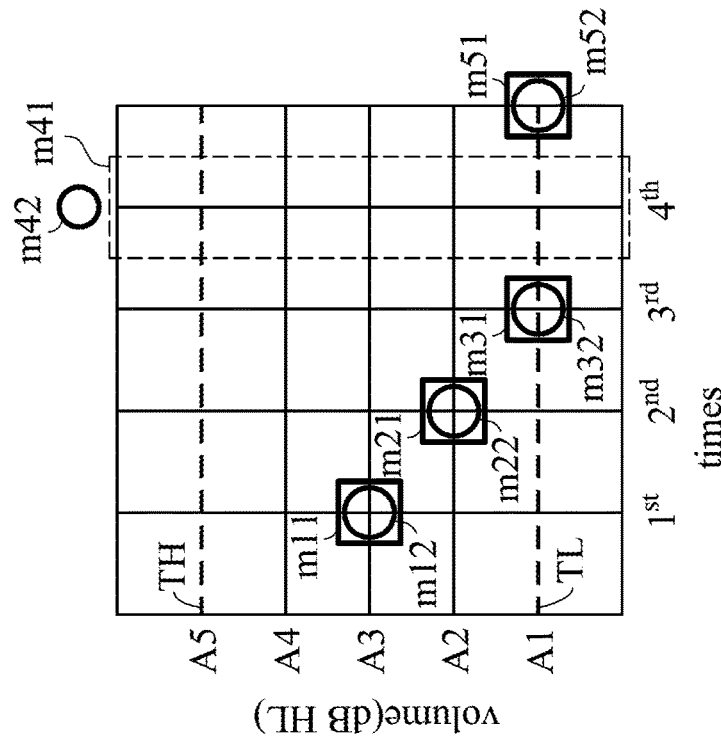
FIGS. 7A-7D illustrate diagrams of feedback status of the same subject for some volumes with blank stimulating sounds at different frequencies, respectively, according to some embodiments of the present disclosure.
Figure 7A:
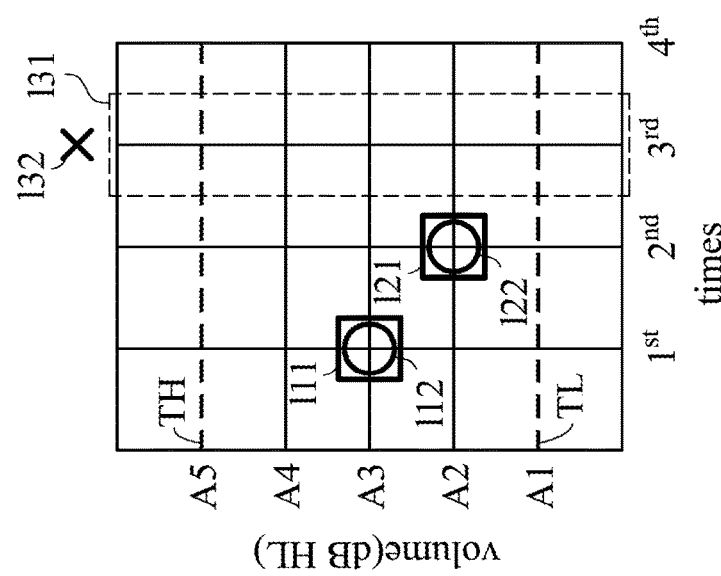

In step S1301, according to an instruction of the control unit 36 of the electronic device 3, the sound generating unit 22 of the assistive listening device 2A is configured to generate testing sounds at a testing frequency. Reference is made to FIG. 7A. FIG. 7A illustrates a diagram of a feedback status of a subject J for some testing sounds with blank stimulating sounds at the frequency F1 according to some embodiments of the present disclosure. As shown in FIG. 7A, the sound generating unit 22 of the assistive listening device 2A is configured to generate testing sounds 111 and 121 at the testing frequency F1 for a subject J. In the embodiment, testing sounds 111 and 121 and feedbacks 112 and 122 are substantially the same as the testing sounds b11 and b21 and the feedbacks b12 and b22 shown in FIG. 3B, respectively, and the related detailed descriptions may refer to the foregoing paragraphs, and are not described again herein.

In step S1302, the control unit 36 of the electronic device 3 is configured to determine whether the subject conducts a feedback on the electronic device 3. When a feedback of the testing sound is of heard for the subject, the hearing test then may proceed to step S1303. Relatively, when a feedback of the testing sound is of unheard for the subject, the hearing test then may proceed to step S1307. That is, the control unit 36 of the electronic device 3 may be configured to selectively increase the volume of a testing sound for the next step and repeat step S1301. For example, in FIG. 7A, a feedback 122 of the testing sound 121 is of heard for the subject J, and then the hearing test may proceed to step S1303.

In step S1303, the control unit 36 of the electronic device 3 is configured to determine whether feedbacks of consecutive two of the testing sounds both are of heard for the subject. When the feedbacks of consecutive two of the testing sounds both are of heard for the subject, the hearing test may then proceed to step S1304. Relatively, when the feedbacks of consecutive two of the testing sounds are not both of heard for the subject, step S1301 is performed again. For example, in FIG. 7A, consecutive two of the feedbacks 112 and 122 of the testing sounds 111 and 121 both are of heard for the subject J, the hearing test then may proceed to step S1304.

In step S1304, the control unit 36 of the electronic device 3 is configured to drive the assistive listening device 2A selectively to perform a blank stimulating sound for the subject to determine the reliability of the hearing test after completing the hearing test of all the test frequencies of the aforementioned ear of the subject (See step S1700 and S1900 of FIG. 2). For example, in FIG. 7A, a blank stimulating sound 131 is set to be performed after consecutive two of the testing sounds 111 and 121. In the embodiment, the blank stimulating sound is not performed directly after the feedback of the testing sound that is of unheard.

In step S1305, the storage unit 30 of the electronic device 3 records that whether the subject responds to the aforementioned blank stimulating sound. For example, in FIG. 7A, the subject J conducts a feedback 132 that is of unheard on the user interface 34 of the electronic device 3 based on the blank stimulating sound 131. The control unit 36 of the electronic device 3 is configured to determine the feedback 132 received by the user interface 34 is of unheard. The storage unit 30 of the electronic device 3 records a number of the feedback of the blank stimulating sound that is of heard (i.e., the feedback 132 of the blank stimulating sound 131 is of unheard and a number of the feedback of the blank stimulating sound that is of heard is zero) for the subject J at the testing frequency F1.

Figure 7D:
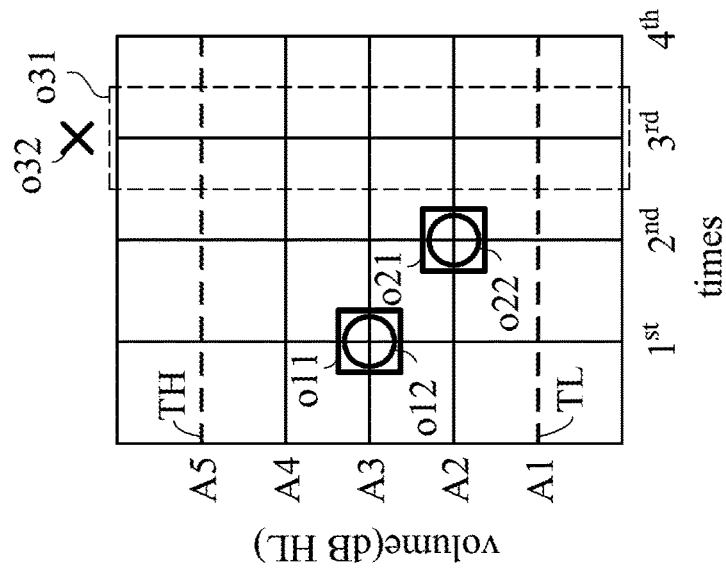
Figure 7C:
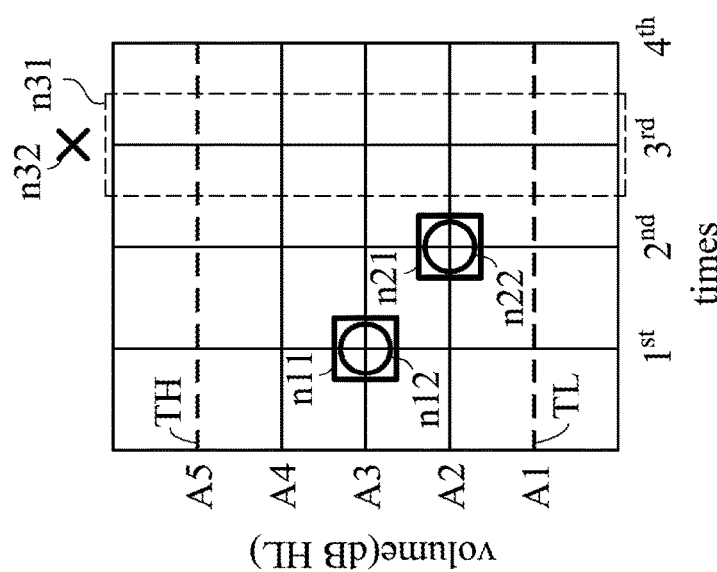

In step S1306, the control unit 36 of the electronic device 3 is configured to determine whether the hearing test of the aforementioned testing frequency is completed. When the hearing test of the aforementioned testing frequency is not completed, the hearing test may then proceed to step S1308, That is, the control unit 36 of the electronic device 3 may be configured to lower the volume of a testing sound for the next step and repeat step S1301. Relatively, when the hearing test of the aforementioned testing frequency is completed, step S1600 and S1700, and/or S1800 of method 1000 for the hearing test shown in FIG. 2 are performed in sequence. In the embodiment, when method 1000 for the hearing test proceeds to step S1800, the aforementioned ear of the subject J completes the hearing test of all testing frequencies. Reference is made to FIGS. 7B-7D. FIGS. 7B-7D illustrate diagrams of feedback status of the subject J for some testing sounds with blank stimulating sounds at different frequencies F2, F3, and F4, respectively, according to some embodiments of the present disclosure.

In FIG. 7B, according to an instruction of the control unit 36 of the electronic device 3, the sound generating unit 22 of the assistive listening device 2A is configured to generate testing sounds m11, m21, and m31 at the testing frequency F2 for the subject J. In the embodiment, the testing sounds m11, m21, and m31 and feedbacks m12, m22, and m32 are substantially the same as the testing sounds b11, b21, and b31 and the feedbacks b12, b22, and b32 shown in FIG. 3B, respectively, and the related detailed descriptions may refer to the foregoing paragraphs, and are not described again herein.

Then, a blank stimulating sound m41 is set to be performed after consecutive two of feedbacks of the testing sounds m21 and m31 that both are of heard. The subject J conducts a feedback m42 of the blank stimulating sound m41 that is of heard on the user interface 34 of the electronic device 3. The control unit 36 of the electronic device 3 is configured to determine the feedback m42 received by the user interface 34 that is of heard, and records a number of the feedback of a blank stimulating sound that is of heard (i.e., the feedback m42 of the blank stimulating sound m41 is of heard and a number of the feedback of the blank stimulating sound that is of heard is one) for the subject J at the testing frequency F2. In the embodiment, the blank stimulating sound m41 may insert between the testing sound m31 and a testing sound m51.

In FIG. 7C, according to an instruction of the control unit 36 of the electronic device 3, the sound generating unit 22 of the assistive listening device 2A is configured to generate testing sounds n11 and n21 at the testing frequency F3 for the subject J. In the embodiment, the testing sounds n11 and n21 and feedbacks n12 and n22 are substantially the same as the testing sounds l11 and l21 and the feedbacks l12 and l22 shown in FIG. 7A, respectively, and the related detailed descriptions may refer to the foregoing paragraphs, and are not described again herein. Then, a blank stimulating sound n31 is set to be performed after consecutive two of the testing sounds n11 and n21. The subject J conducts a feedback n32 of the blank stimulating sound n31 that is of unheard on the user interface 34 of the electronic device 3. The control unit 36 of the electronic device 3 is configured to determine the feedback n32 received by the user interface 34 is of unheard, and records a number of the feedback of a blank stimulating sound that is of heard (i.e., the feedback n32 of the blank stimulating sound n31 is of unheard and a number of the feedback of the blank stimulating sound that is of heard is zero) for the subject J at the testing frequency F3.

In FIG. 7D, according to an instruction of the control unit 36 of the electronic device 3, the sound generating unit 22 of the assistive listening device 2A is configured to generate testing sounds o11 and o21 at the testing frequency F4 for the subject J. In the embodiment, the testing sounds o11 and o21 and feedbacks o12 and o22 are substantially the same as the testing sounds l11 and l21 and the feedbacks l12 and l22 shown in FIG. 7A, respectively, and the related detailed descriptions may refer to the foregoing paragraphs, and are not described again herein. Then, a blank stimulating sound o31 is set to be performed after consecutive two of the testing sounds o11 and o21. The subject J conducts a feedback o32 of the blank stimulating sound o31 that is of unheard on the user interface 34 of the electronic device 3. The control unit 36 of the electronic device 3 is configured to determine the feedback o32 received by the user interface 34 is of unheard, and records a number of the feedback of a blank stimulating sound that is of heard (i.e., the feedback o32 of the blank stimulating sound o31 is of unheard and a number of the feedback of the blank stimulating sound that is of heard is zero) for the subject J at the testing frequency F4

Reference is made to FIG. 2. Method 1000 for the hearing test then proceeds to step S1900. In step S1900, when a number of the feedbacks of the subject that are of heard is greater than a number of the feedbacks of the subject that are of unheard in all of the blank stimulating sounds, the aforementioned method 1000 for the hearing test is of the poor reliability, and the hearing test may then proceed to step S2400. Relatively, when a number of the feedbacks of the subject that are of heard is less than or substantially equals to a number of the feedbacks of the subject that are of unheard in all of the blank stimulating sounds, the aforementioned method 1000 for the hearing test is of the acceptable reliability, and the hearing test may then proceed to step S2100.

For example, as shown in FIGS. 7A-7D, after the aforementioned ear of the subject J completes the hearing test for all test frequencies, a number of the feedbacks to all the blank stimulating sounds that is of heard is one, and a number of the feedbacks to all the blank stimulating sounds that is of unheard is three. The number of the feedbacks to all the blank stimulating sounds that is of heard is less than the number of the feedbacks to all the blank stimulating sounds that is of unheard, so method 1000 for the hearing test is classified as the acceptable reliability, and the hearing test may then proceed to step S2100. Specifically, Table. 3 shows the result of the reliability of the self-hearing test performed by one of the ears of the subject J, as shown below.

TABLE 3 the result of the reliability of the self-hearing test performed by one of the ears of the subject J

| number of blank stimulating sounds (N5) | number of feedback that is of heard based on blank stimulating sound (N6) | N6/N5 | N6/N5 > 50% (Y/N) | acceptable reliability or poor reliability |
|---|---|---|---|---|
| 4 | 1 | 25% | N | acceptable reliability |

Figure 8:
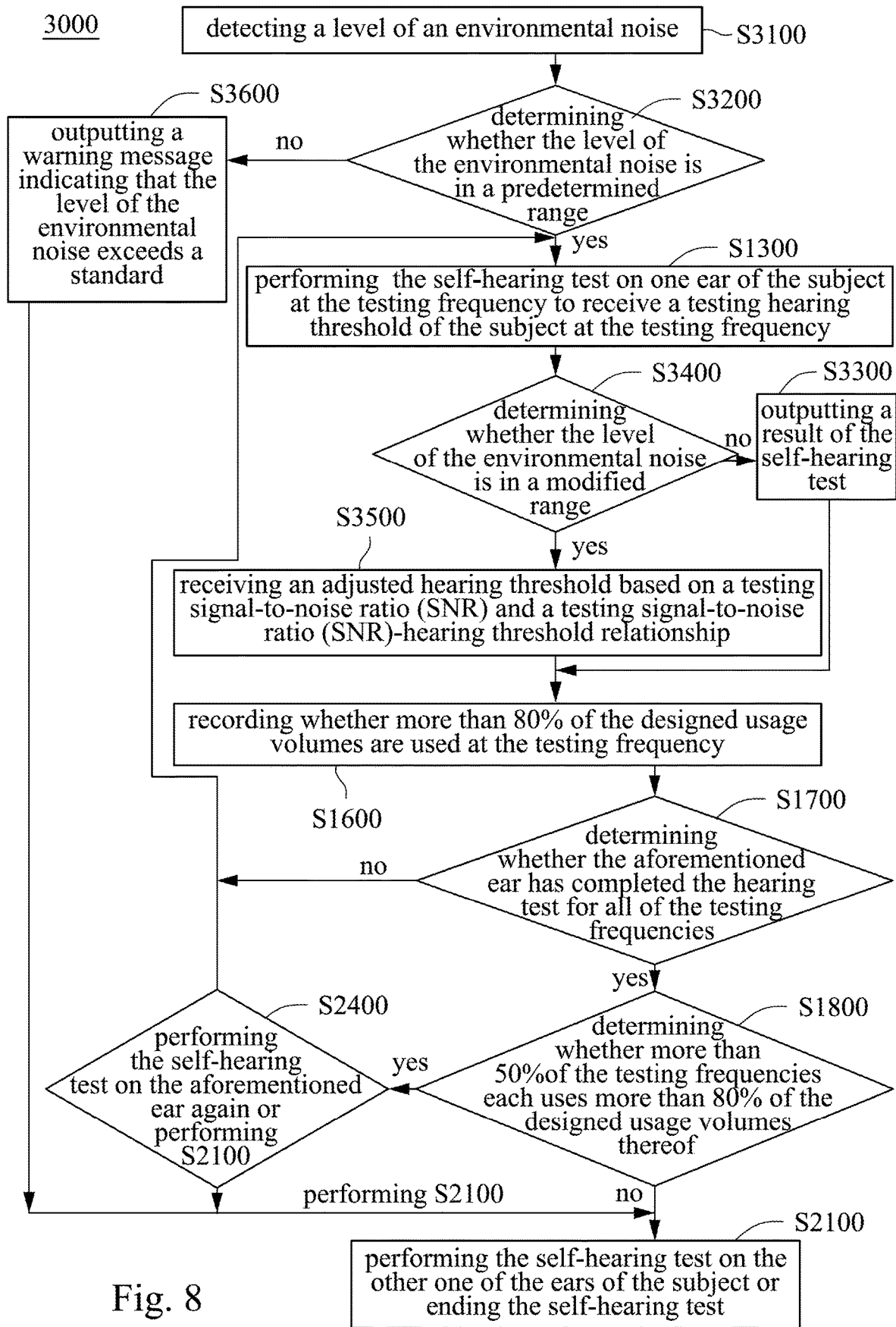
FIG. 8 illustrates a flowchart of a method for a hearing test under a noise environment according to some embodiments of the present disclosure.

Reference is made to FIG. 8. FIG. 8 illustrates a flowchart of method 3000 for a hearing test under a noise environment according to some embodiments of the present disclosure.

It is understood that method 3000 shown in FIG. 8 has been simplified for a better understanding of the embodiments of the present disclosure. Accordingly, additional processes may be provided before, during, and after the stages of method 3000 shown in FIG. 8, and some other processes may be briefly described herein. Specifically, method 3000 for the hearing test includes step S1300 to step S3600.

In FIG. 8, method 3000 for the hearing test is substantially the same as method 1000 for the hearing test shown in FIG. 2, and the related detailed descriptions may refer to the foregoing paragraphs, and are not described again herein. It is noted that, the difference between the present embodiment and the embodiment in FIG. 2 is in that, method 3000 for the hearing test is applied to noise environment and further includes steps S3100, S3200, S3400, S3500, S3300, and S3600, and step S1900 is omitted.

In the embodiment, method 3000 for the hearing test begins at step S3100. In step S3100, the sound detecting unit 20 of the assistive listening device 2A is configured to detect a level of an environmental noise at a testing frequency in a testing environment where the subject is located. For example, the sound detecting unit 20 of the assistive listening device 2A is configured to detect a level of an environmental noise at the testing frequency F2 in a testing environment where a subject Q is located. In the embodiment, an environmental noise at the testing frequency F2 may be referred to as a noise at a specific frequency. In the embodiment, the testing frequency F2 may be about 1 kHz, and a level of the noise at the testing frequency F2 may be about 70 dB sound pressure level (SPL), but the present disclosure is not limited thereto.

Reference is made to FIG. 8. Method 3000 for the hearing test then proceeds to step S3200. In step S3200, the assistive listening device 2A is configured to transmit the detected level of the environmental noise to the electronic device 3 via the wireless transmission unit 28. Then, the control unit 36 of the electronic device 3 may be configured to determine whether the level of the environmental noise at each testing frequency is in a predetermined range (may also be referred to as an acceptable range). When the level of the environmental noise is out of the acceptable range (See table. 4) at one of the testing frequencies, step S3600 and step S2100 are sequentially performed, of which step S3600 is performed to output a warning message indicating that the level of the environmental noise exceeds a standard to the user interface 34 of the electronic device 3 to warn the subject, and step S2100 is performed to perform a self-hearing test on the other one of the ears of the subject or to end the self-hearing test.

Relatively, when a level of an environmental noise is in the acceptable region (See table. 4) at each of the testing frequencies, the hearing test may then proceed to step S1300. For example, when a level of an environmental noise at the testing frequency F2 is detected to be about 70 dB SPL and within the acceptable region (See table. 4), the hearing test may then proceed to step S1300. Specifically, Table. 4 shows the ranges of the levels of the environmental noise at the different frequencies that can be accepted by the hearing test method, as shown below.

TABLE 4 the ranges of the levels of the environmental noise at the different frequencies that can be accepted by the hearing test method

| | frequency of the noise (Hz) | | | |
|---|---|---|---|---|
| | 500 | 1000 | 2000 | 4000 |
| range of acceptable volume of noise (dB SPL) | 41~70 | 38~70 | 39~70 | 36~77 |

In some embodiments, the level of the environmental noise at each testing frequency can be converted from the sound pressure level (SPL) to a hearing level (HL) by the control unit 36 of the electronic device 3. For example, at the testing frequency F2, an environmental noise at the sound pressure level of about 70 dB can be converted to at the hearing level of about 62.5 dB.

Furthermore, the assistive listening device 2A of the hearing test system 1 has a noise attenuation value of about 20 dB at the testing frequency F2, but the present disclosure is not limited thereto. When an environmental noise passes through the assistive listening device 2A to lose a part of the energy thereof, a background noise level lower than the level of the environmental noise may be formed inside of the assistive listening device 2A close to the subject. For example, at the testing frequency F2, an environmental noise of about 62.5 dB HL may form a background noise level of about 42.5 dB HL after passing through the assistive listening device 2A. Therefore, when the assistive listening device 2A is configured to generate the testing sounds at the testing frequency F2, the subject Q may simultaneously receive a background noise level formed by an environmental noise and receive a volume of a testing sound.

Reference is made to FIG. 8. Method 3000 for the hearing test then proceeds to step S1300. In step S1300, the self-hearing test is performed on one of the subject's ears at a background noise level formed by the aforementioned noise environment to obtain the testing hearing threshold of the subject at the aforementioned testing frequency, in which the method of obtaining the testing hearing threshold can refer to step S1300 of method 1000 for the hearing test shown in FIG. 2.

Reference is made to FIG. 8. Method 3000 for the hearing test then proceeds to step S3400. In step S3400, the control unit 36 of the electronic device 3 is configured to determine whether a level of an environmental noise is in a modified range. When a level of an environmental noise is in the modified range, the hearing test may then proceed to step S3500. When a level of an environmental noise is out of the modified range, step S3300 and step S1600 are sequentially performed, in which step S3300 is performed to output the result of the self-hearing test to the electronic device 3, and step S1600 is performed to record whether more than 80% of the designed usage volumes is used for each of the testing frequency.

Figure 9:
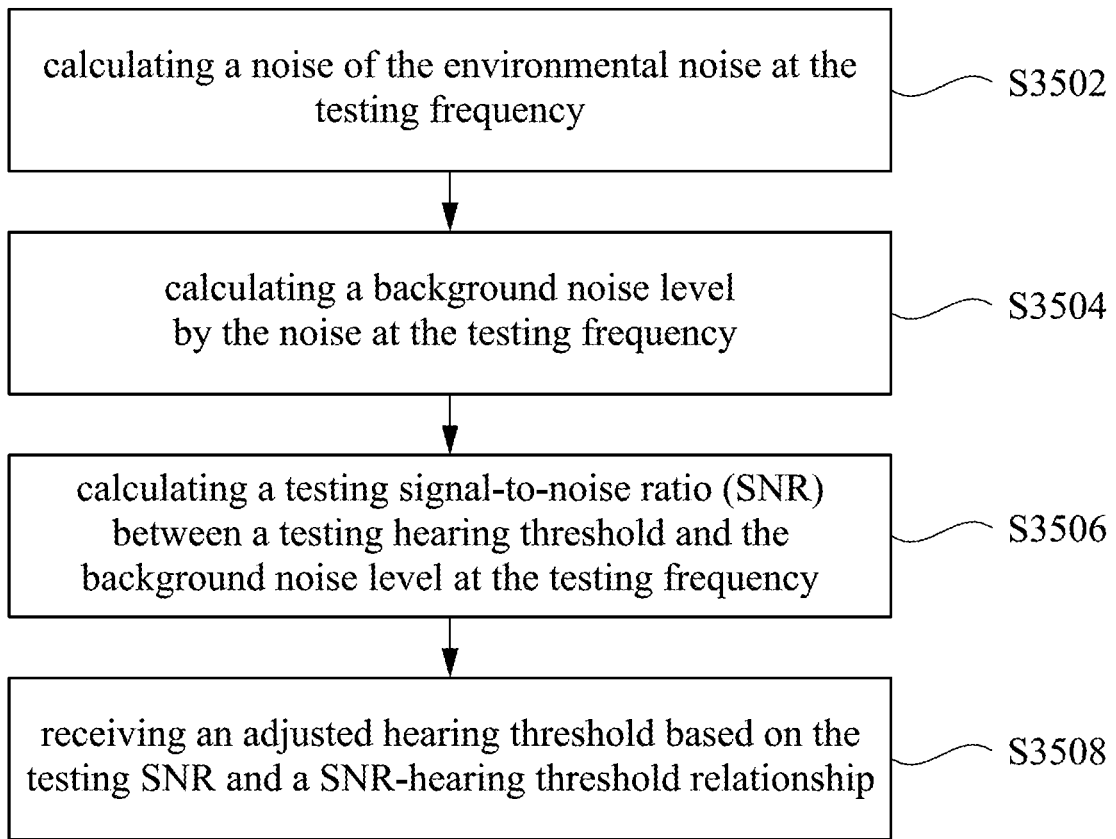
FIG. 9 illustrates a flowchart of a method for receiving an adjusted hearing threshold according to some embodiments of the present disclosure.

Reference is made to FIG. 8. Method 3000 for the hearing test then proceeds to step S3500. In step S3500, the control unit 36 of the electronic device 3 is configured to receive an adjusted hearing threshold based on a testing signal-to-noise ratio (SNR) and a testing signal-to-noise ratio (SNR)-hearing threshold relationship. Reference is made to FIG. 9. FIG. 9 illustrates a flowchart of step S3500 for receiving an adjusted hearing threshold according to some embodiments of the present disclosure.

It is understood that step S3500 shown in FIG. 9 has been simplified for a better understanding of the embodiments of the present disclosure. Accordingly, additional processes may be provided before, during, and after the stages of step S3500 shown in FIG. 9, and some other processes may be briefly described herein. Specifically, step S3500 further includes step S3502 to step S3508.

In step S3502, the control unit 36 of the electronic device 3 is configured to calculate a noise of an environmental noise at the testing frequency. For example, a level of a noise of an environmental noise at the testing frequency F2 may be about 62.5 dB HL, but the present disclosure is not limited thereto.

In step S3504, the control unit 36 of the electronic device 3 is configured to calculate a second background noise level by the noise at the testing frequency. For example, at the testing frequency F2, an environmental noise of about 62.5 dB HL may form a background noise level of about 42.5 dB HL after passing through the assistive listening device 2A.

In step S3506, the control unit 36 of the electronic device 3 is configured to calculate the testing signal-to-noise ratio between the testing hearing threshold and a background noise level at the testing frequency F2. For example, the testing hearing threshold of the subject Q may be about 40 dB HL at the testing frequency F2, and the second background noise level may be about 42.5 dB HL at the testing frequency F2. The control unit 36 of the electronic device 3 is configured to calculate a testing signal-to-noise ratio SNR2 of the subject Q of about 2.5 dB at the testing frequency F2 by the testing hearing threshold of and the second background noise level.

In step S3508, the storage unit 30 of the electronic device 3 is configured to store a SNR-hearing threshold relationship at a testing frequency. The control unit 36 of the electronic device 3 is configured to receive an adjusted hearing threshold based on a testing signal-to-noise ratio and the SNR-hearing threshold relationship. Reference is made to FIG. 10B. FIG. 10B illustrates the experimental result of signal-to-noise ratios versus hearing thresholds at the frequency F2, respectively, in a noise environment according to some embodiments of the present disclosure, in which the experimental result is obtained using the hospital's measuring instruments.

For example, when the testing signal-to-noise ratio SNR2 of the subject Q at the testing frequency F2 is about −2.5 dB, the control unit 36 of the electronic device 3 is configured to calculate a corresponding adjusted hearing threshold S2 from the testing signal-to-noise ratio SNR2 to be about 35 dB HL through a SNR-hearing threshold relationship R2 shown in FIG. 10B. In other words, a hearing test result of the first testing frequency can be modified by a first adjusted hearing threshold. In the embodiment, the adjusted hearing threshold S2 may be less than the testing hearing threshold. Specifically, Table. 5 shows the result of the adjusted hearing threshold of the subject Q at the testing frequency F2, as shown below.

TABLE 5 the result of the adjusted hearing threshold
of the subject Q at the testing frequency F2

| | | | | |
|---|---|---|---|---|
| level of environmental noise (dB SPL) | 70 | 70 | 70 | 70 |
| level of environmental noise (dB HL) | 62.5 | 62.5 | 62.5 | 62.5 |
| noise attenuation value (dB) | 20 | 20 | 20 | 20 |
| background noise level (dB HL) | 42.5 | 42.5 | 42.5 | 42.5 |
| volume of testing sound(dB HL) | 25 | 30 | 35 | 40 |
| feedback of subject (heard(○)/unheard (X)) | X | X | X | ○ |
| signal-to-noise ratio (dB) | −17.5 | −12.5 | −7.5 | −2.5 |
| adjusted hearing threshold (dB HL) | | | | 35 |

For example, when the testing signal-to-noise ratio SNR2 of a subject R at the testing frequency F2 is about −7.5 dB, the control unit 36 of the electronic device 3 is configured to calculate a corresponding adjusted hearing threshold S2 from the testing signal-to-noise ratio SNR2 to be about 30 dB HL through the SNR-hearing threshold relationship R2 shown in FIG. 10B. In other words, a hearing test result of the first testing frequency can be modified by the first adjusted hearing threshold. Specifically, Table. 6 shows the result of the adjusted hearing threshold of the subject R at the testing frequency F2, as shown below.

TABLE 6 the result of the adjusted hearing threshold
of the subject R at the testing frequency F2

| | | | | |
|---|---|---|---|---|
| level of environmental noise (dB SPL) | 70 | 70 | 70 | 70 |
| level of environmental noise (dB HL) | 62.5 | 62.5 | 62.5 | 62.5 |
| noise attenuation value (dB) | 20 | 20 | 20 | 20 |
| background noise level (dB HL) | 42.5 | 42.5 | 42.5 | 42.5 |
| volume of testing sound(dB HL) | 25 | 30 | 35 | 40 |
| feedback of subject (heard (○)/unheard (X)) | X | X | ○ | ○ |
| signal-to-noise ratio (dB) | −17.5 | −12.5 | −7.5 | −2.5 |
| adjusted hearing threshold (dB HL) | | | 30 | |

Specifically, the SNR-hearing threshold relationship R2 may be a linear regression relation, and is obtained from samples with multiple signal-to-noise ratios relative to hearing thresholds based on multiple patients with moderate hearing loss in a noise environment at the testing frequency F2. In the embodiment, a number of samples with the signal-to-noise ratio to the hearing thresholds in the noise environment at the testing frequency F2 is about 50, but the present disclosure is not limited thereto.

In FIG. 10B, the SNR-hearing threshold relationship R2 includes an upper SNR boundary UB2 and a lower SNR boundary LB2. The upper SNR boundary UB2 is an upper boundary formed by multiple signal-to-noise ratios relative to hearing thresholds based on multiple patients with moderate hearing loss in a noise environment at the testing frequency F2. The lower SNR boundary LB2 is a lower boundary formed by multiple signal-to-noise ratios relative to hearing thresholds based on multiple patients with moderate hearing loss in a noise environment at the testing frequency F2. In the embodiment, a difference between any data point in the SNR-hearing threshold relationship R2 and the lower SNR boundary LB2 is greater than a difference between the any data point in the SNR-hearing threshold relationship R2 and the upper SNR boundary UB2.

Reference is made to FIG. 8. Method 3000 for the hearing test then proceeds to step S1600. In step S1600, in a noise environment, the storage unit 30 of the electronic device 3 is configured to record whether more than 80% of the designed usage volumes is used for the aforementioned testing frequency, to further determine a reliability of the hearing test by the control unit 36, in which method of comparing a number of the designed usage volumes and a number of the actual usage volumes at a testing frequency can refer to step S1600 of method 1000 for the hearing test shown in FIG. 2.

Reference is made to FIG. 8. Method 3000 for the hearing test then proceeds to step S1700. In step S1700, in the noise environment, the control unit 36 of the electronic device 3 is configured to determine whether the aforementioned ear has completed the respective hearing test of all testing frequencies, in which method of determining can refer to step S1700 of method 1000 for the hearing test shown in FIG. 2.

In the embodiment, under the background noise level formed by the aforementioned noise environment, method 3000 for the hearing test is also designed to perform the self-hearing tests on the aforementioned ear of the subject Q at the different testing frequencies F1, F3, and F4 to obtain the testing hearing thresholds of the subject Q at the testing frequencies F1, F3, and F4, respectively. The storage unit 30 of the electronic device 3 is configured to store SNR-hearing threshold relationships R1, R3, and R4 (See FIGS. 10A, 10C, and 10D) at the testing frequencies F1, F3, and F4, respectively, and to obtain adjusted hearing thresholds S1, S3, and S4 based on testing signal-to-noise ratios SNR1, SNR3, and SNR4 at the testing frequencies F1, F3, and F4 and the SNR-hearing threshold relationships R1, R3, and R4.

For example, the testing hearing threshold of the subject Q is obtained under a first background noise level at the testing frequency F1. Then, the testing signal-to-noise ratio SNR1 between a testing hearing threshold and the first background noise level at the testing frequency F1 is calculated. Then, the first adjusted hearing threshold S1 different from the second adjusted hearing threshold S2 is obtained based on the testing signal-to-noise ratio SNR1 and the SNR-hearing threshold relationship R1. Then, the hearing test result of the first testing frequency is modified based on the first adjusted hearing threshold S1. In the embodiment, the first adjusted hearing threshold S1 may be less than a first testing hearing threshold.

Figure 10C:
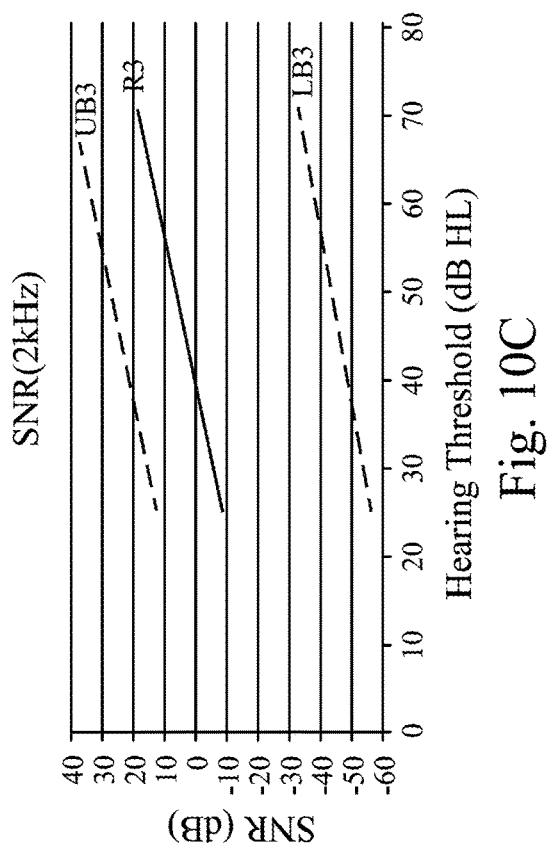
FIGS. 10A-10D illustrate experimental results of signal-to-noise ratios versus hearing thresholds at different frequencies, respectively, in a noise environment according to some embodiments of the present disclosure.
Figure 10D:
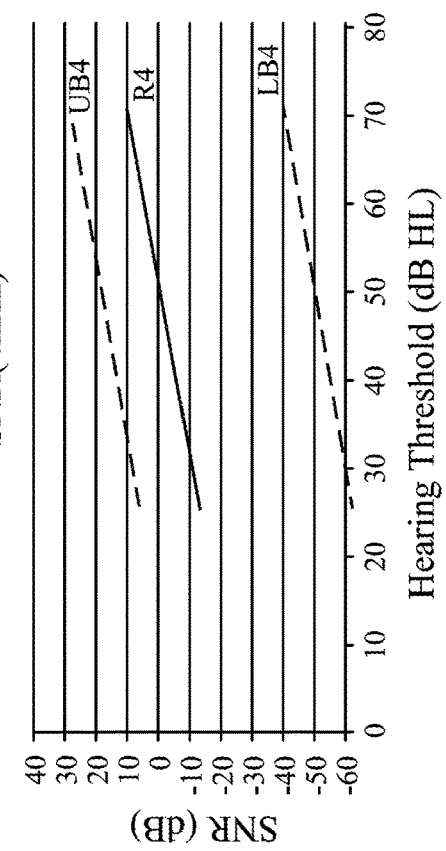
Figure 10A:
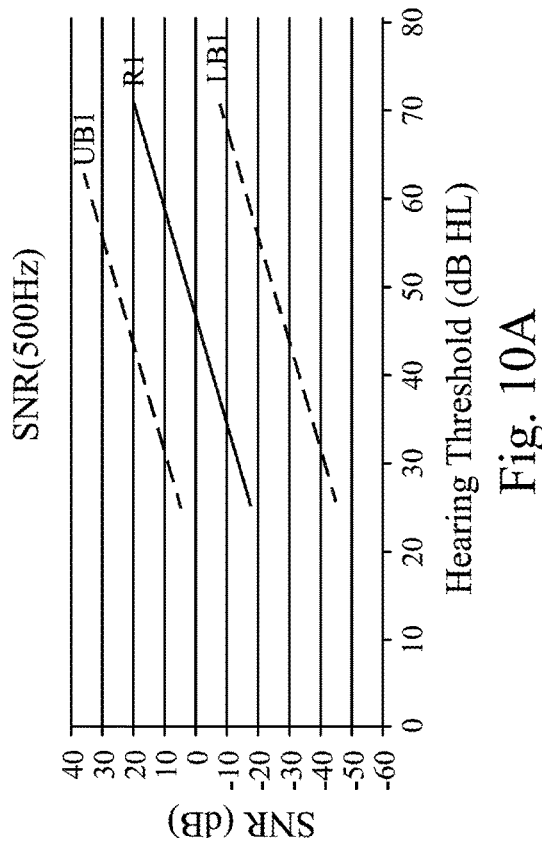
Figure 10B:
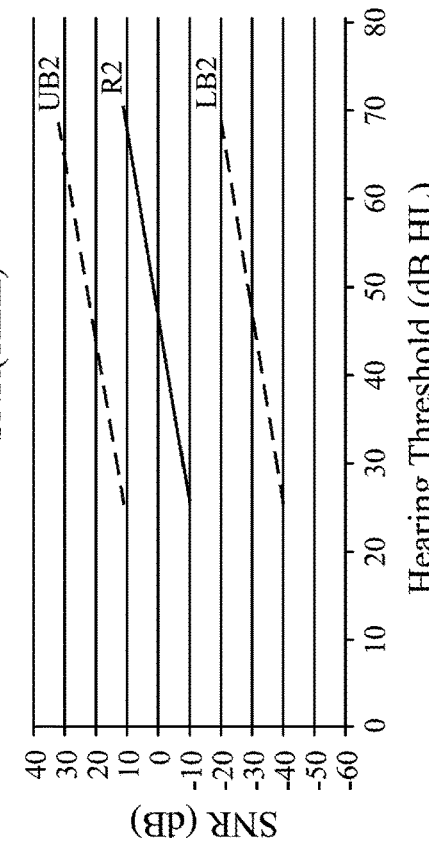

Reference is made to FIGS. 10A, 10C, and 10D. FIGS. 10A, 10C, and 10D illustrate experimental results of signal-to-noise ratios versus hearing thresholds at the different frequencies F1, F3, and F4, respectively, in a noise environment according to some embodiments of the present disclosure, in which the experimental results are obtained using the hospital's measuring instruments.

In FIG. 10A, the SNR-hearing threshold relationship R1 includes an upper SNR boundary UB1 and a lower SNR boundary LB1. In FIG. 10C, a SNR-hearing threshold relationship R3 includes an upper SNR boundary UB3 and a lower SNR boundary LB3. In FIG. 10D, a SNR-hearing threshold relationship R4 includes an upper SNR boundary UB4 and a lower SNR boundary LB4.

In some embodiments, a first difference between any data point in a first SNR-hearing threshold relationship at a first testing frequency and a first lower SNR boundary thereof is different from a second difference between any data point in a second SNR-hearing threshold relationship at a second testing frequency and a second lower SNR boundary thereof, in which at the first testing frequency is different from at the second testing frequency. For example, when the testing frequency F2 is greater than the testing frequency F1, a difference between any data point in the SNR-hearing threshold relationship R1 and the lower SNR boundary LB1 thereof shown in FIG. 10A may be less than a difference between any data point in the SNR-hearing threshold relationship R2 and the lower SNR boundary LB2 thereof shown in FIG. 10B.

Reference is made to FIG. 8. Method 3000 for the hearing test then proceeds to step S1800. In step S1800, the control unit 36 of the electronic device 3 is configured to determine whether more than 50% of the testing frequencies each is used more than 80% of the designed usage volumes thereof, in which method of determining can refer to step S1800 of method 1000 for the hearing test shown in FIG. 2.

Reference is made to FIG. 8. Method 3000 for the hearing test then proceeds to step S2100. Step S2100 is performed to perform a the self-hearing test on the other one of the ears of the subject or to end the self-hearing test, in which method of performing can refer to step S2100 of method 1000 for the hearing test shown in FIG. 2.

Reference is made to FIG. 8. Method 3000 for the hearing test then proceeds to step S2400. In step S2400, the subject determines to perform the self-hearing test on the aforementioned ear again or to perform the next step (i.e., step S2100), in which the method of performing can refer to step S2400 of method 1000 for the hearing test shown in FIG. 2.

In the embodiment, after the subject completed method 1000 and method 3000 for the self-hearing test as shown in FIGS. 2 and 8, the control unit 36 of the electronic device 3 is configured to modify a testing sound stored in the electronic device 3 according to a testing hearing threshold or an adjusted hearing threshold obtained from method 1000 or method 3000 for the self-hearing test. Then, the sound generating unit 32 of the electronic device 3 is configured to generate the modified testing sound for the subject. After the assistive listening devices 2A and 2B worn on two ears of a subject is configured to receive the modified testing sound, the assistive listening devices 2A and 2B may transmit the modified testing sound to the control unit 36 of the electronic device 3 to perform an analysis, so as to further modify a distance between the electronic device 3 and the assistive listening device 2A and modify a distance between the electronic device 3 and the assistive listening device 2B.

Then, after a positional relationship between the electronic device 3 and the assistive listening devices 2A and 2B is adjusted, the sound generating unit 32 of the electronic device 3 is configured to generate the modified testing sound for a subject P, causes the subject P to determine whether the modified testing sound can be directly accepted by the ears thereof. Then, the subject P determines whether to re-test method 1000 or method 3000 for the hearing test to obtain a new testing hearing threshold or a new adjusted hearing threshold to re-modify the testing sound, or determines to directly use a testing hearing threshold or an adjusted hearing threshold to modify volume conversion parameters in the assistive listening devices 2A and 2B and further to directly use the modified assistive listening devices 2A and 2B.

Figure 11:
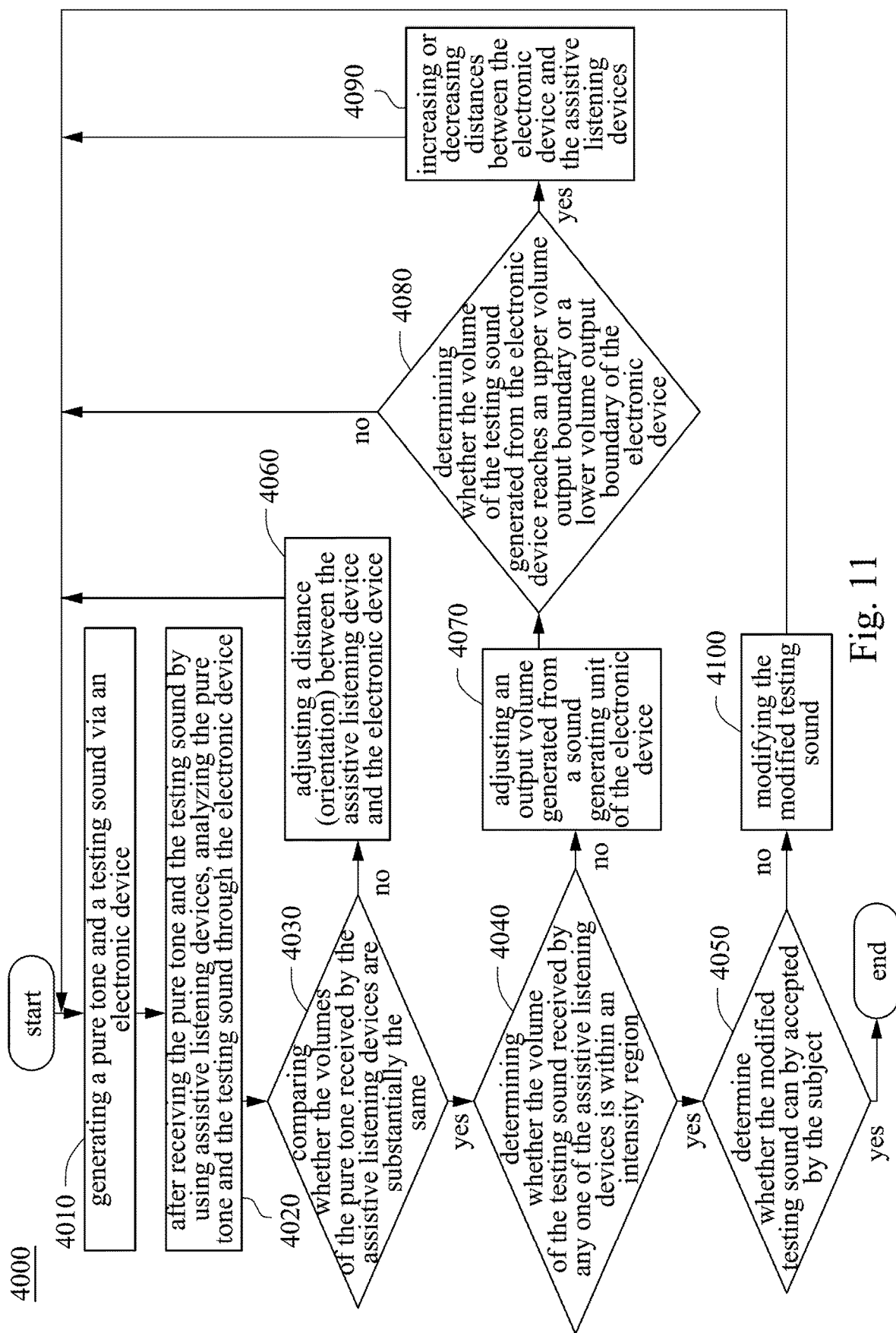
FIG. 11 illustrates a flowchart of a method for a hearing test according to some embodiments of the present disclosure.

Specifically, reference is made to FIG. 11. FIG. 11 illustrates a flowchart of method 4000 for a hearing test according to some embodiments of the present disclosure. It is understood that method 4000 shown in FIG. 11 has been simplified for a better understanding of the embodiments of the present disclosure. Accordingly, additional processes may be provided before, during, and after the stages of method 4000 shown in FIG. 11, and some other processes may be briefly described herein.

Specifically, method 4000 for the hearing test includes step S4010 to step S4100. In the embodiment, method 4000 for the hearing test is performed by applying the hearing test system 1 as shown in FIG. 1.

Method 4000 for the hearing test begins at step S4010. In step S4010, the sound generating unit 32 of the electronic device 3 is configured to generate a pure tone and the modified testing sound. Specifically, a signal generated by the sound generating unit 32 includes the pure tone and includes the modified testing sound with multiple testing frequencies.

In the embodiment, the subject receives the modified testing sound which is modified from a testing sound stored in the control unit 36 of the electronic device 3 by a testing hearing threshold or an adjusted hearing threshold which obtained by method 1000 and method 3000 for the self-hearing test as shown in FIGS. 2 and 8.

In the embodiment, volumes of the modified testing sound at the multiple testing frequencies all may be less than a volume of the pure tone. For example, volumes of the modified testing sound at the multiple testing frequencies each may be at least less about 3 dB than a volume of the pure tone, such that the subject P may distinguish the pure tone and the modified testing sound. In some embodiments, a frequency of the pure tone may be in a range from about 250 Hz to about 8000 Hz, but the present disclosure is not limited thereto.

In the embodiment, the pure tone and the modified testing sound may be simultaneously generated by the sound generating unit 32 of the electronic device 3, but the present disclosure is not limited thereto. In some embodiments, the sound generating unit 32 of the electronic device 3 may be configured to generate the pure tone first, and a distance between the electronic device 3 and the assistive listening device 2A and a distance between the electronic device 3 and the assistive listening device 2B may be modified by the pure tone. Then, the sound generating unit 32 may be configured to generate the modified testing sound, and the modified distance between the electronic device 3 and the assistive listening device 2A and the modified distance between the electronic device 3 and the assistive listening device 2B may be further modified by the modified testing sound, of which the foregoing method of modification may be described in step S4060 and step S4090 of method 4000 for the hearing test.

Reference is made to FIG. 11. Method 4000 for the hearing test then proceeds to step S4020. In step S4020, after receiving the pure tone and modified testing sound by using at least one assistive listening device, analyzing the pure tone and the modified testing sound received by the at least one assistive listening device through the electronic device 3. Specifically, the assistive listening device 2A is configured to detect a first intensity of the signal generated by the electronic device 3. The assistive listening device 2B is configured to detect a second intensity of the signal generated by the electronic device 3. The assistive listening device 2A and the assistive listening device 2B are respectively worn in the ears of the subject P, thereby substantially maintaining a fixed distance D1 (See FIG. 12A).

Then, the assistive listening device 2A and the assistive listening device 2B each is configured to respectively transmit a volume of the received pure tone and a volume of the modified testing sound to the wireless transmission unit 38 of the electronic device 3 via the wireless transmission unit 28, and further transmit to the control unit 36 of the electronic device 3. The control unit 36 is configured to analyze the volumes of pure tone and the volumes of the modified testing sound received by the assistive listening device 2A and the assistive listening device 2B.

Reference is made to FIG. 11. Method 4000 for the hearing test then proceeds to step S4030. In step S4030, the control unit 36 of the electronic device 3 is configured to compare whether the volumes of the pure tone received by the multiple assistive listening devices are substantially the same. For example, when the volumes of the pure tone received by the assistive listening device 2A and the assistive listening device 2B are substantially the same, the hearing test may then proceed to step S4040. Relatively, when the volumes of the pure tone received by the assistive listening device 2A and the assistive listening device 2B are different, the hearing test may then proceed to step S4060.

Reference is made to FIG. 11. Method 4000 for the hearing test then proceeds to step S4040. In step S4040, the control unit 36 of the electronic device 3 is configured to determine whether the volume of the modified testing sound received by any one of the assistive listening devices is within an intensity region. For example, when the volume of the modified testing sound received by the assistive listening device 2A and/or the assistive listening device 2B is within the intensity region, the hearing test may then proceed to step S4050. Relatively, when the volume of the modified testing sound received by the assistive listening device 2A and/or the assistive listening device 2B is out of the intensity region, the hearing test may then proceed to step S4070. In the embodiment, the intensity region may be in a range from about 50 dB to about 80 dB, but the present disclosure is not limited thereto.

Reference is made to FIG. 11. Method 4000 for the hearing test then proceeds to step S4050. In step S4050, the control unit 36 of the electronic device 3 is configured to determine whether the modified testing sound can be accepted by the subject P. For example, when the modified testing sound is accepted by the subject P, method 4000 for the hearing test may be terminated. In the embodiment, the subject P can directly modify the volume conversion parameters in the assistive listening devices 2A and 2B by using the testing hearing threshold or the adjusted hearing threshold obtained by method 1000 or method 3000 for the self-hearing test, and then can directly use the modified the assistive listening devices 2A and 2B to assist the hearing thereof.

Relatively, when the modified testing sound is not accepted by the subject P, the hearing test may then proceed to step S4100. In step S4100, the modified testing sound is further modified. That is, the subject P re-tests method 1000 or method 3000 for the hearing test to obtain a new testing hearing threshold or a new adjusted hearing threshold to re-modify the testing sound.

Reference is made to FIG. 11. Method 4000 for the hearing test then proceeds to step S4060. In step S4060, a distance (or an orientation) between the assistive listening device and an electronic device may be adjusted. In the embodiment, in order to allow the assistive listening device 2A and the assistive listening device 2B worn on the ears of the subject P to obtain substantially the same volumes of the pure tone generated from the electronic device 3, the subject P may move (referring to FIGS. 12A and 12B) the electronic device 3 relative to the assistive listening device 2A and the assistive listening device 2B, or may rotate (referring to FIGS. 13A-15B) the assistive listening device 2A and the assistive listening device 2B based on an axis (e.g., the subject P). As such, a distance between the assistive listening device 2A and the electronic device 3 may be substantially the same as a distance between the assistive listening device 2B and the electronic device 3, and thus the assistive listening device 2A and the assistive listening device 2B may receive substantially the same volumes from the sound generating unit 32 of the electronic device 3.

Figure 12B:
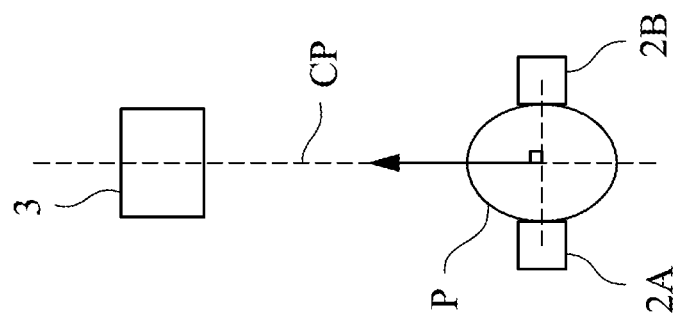
FIGS. 12A and 12B illustrate schematic diagrams of different intermediate stages of a method for a hearing test including assistive listening devices, electronic device, and a subject according to some embodiments of the present disclosure.
Figure 12A:
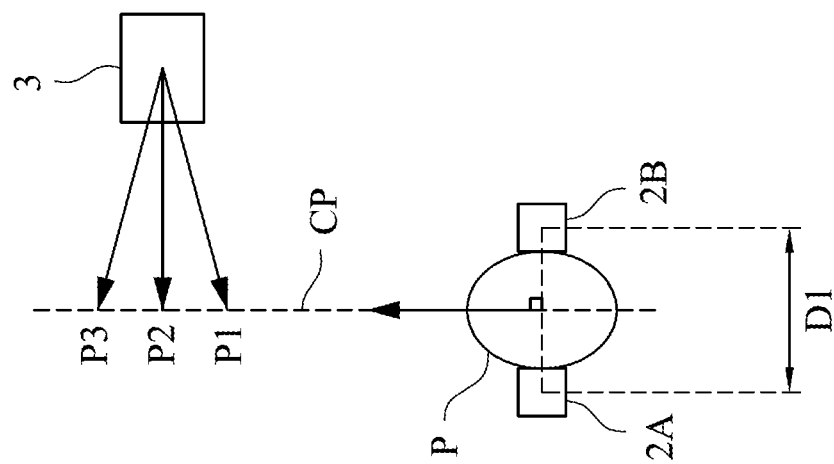

Reference is made to FIGS. 12A and 12B. FIGS. 12A and 12B illustrate schematic diagrams of different intermediate stages of method 4000 for a hearing test including the assistive listening devices 2A and 2B, the electronic device 3, and a subject P according to some embodiments of the present disclosure, in which the subject P is a subject who has passed method 1000 or method 3000 for the hearing test to obtain a testing hearing threshold or an adjusted hearing threshold.

Since the electronic device 3 is not located on a midperpendicular plane CP of a virtual connection line between the assistive listening device 2A and the assistive listening device 2B, a distance between the assistive listening device 2A and the electronic device 3 is different from a distance between the assistive listening device 2B and the electronic device 3, and thus the assistive listening device 2A and the assistive listening device 2B may configured to receive different volumes of the pure tone.

Then, the electronic device 3 is configured to move toward the midperpendicular plane CP of the virtual connection line between the assistive listening device 2A and the assistive listening device 2B to adjust the distance between the assistive listening device 2A and the electronic device 3 and the distance between the assistive listening device 2B and the electronic device 3. For example, the electronic device 3 may be configured to move toward a position P1, a position P2, or a position P3 located on the midperpendicular plane CP. When the electronic device 3 is configured to located on the midperpendicular plane CP, the distance between the assistive listening device 2A and the electronic device 3 may be substantially the same as the distance between the assistive listening device 2B and the electronic device 3, and thus the assistive listening device 2A and the assistive listening device 2B may be configured to receive substantially the same volumes from the sound generating unit 32 of the electronic device 3.

Figure 13B:
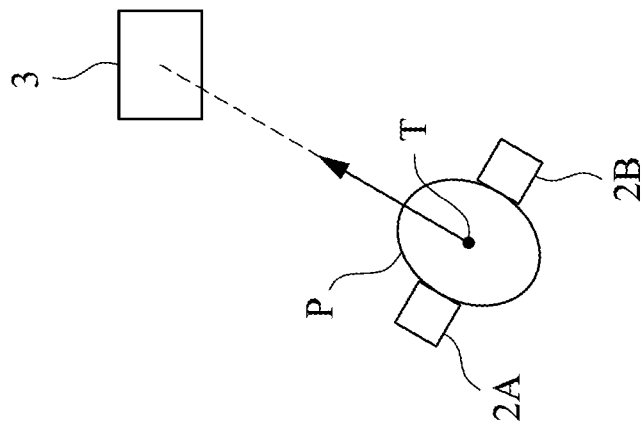
FIGS. 13A and 13B illustrate schematic diagrams of different intermediate stages of a method for a hearing test including assistive listening devices, electronic device, and a subject according to some embodiments of the present disclosure.
Figure 13A:
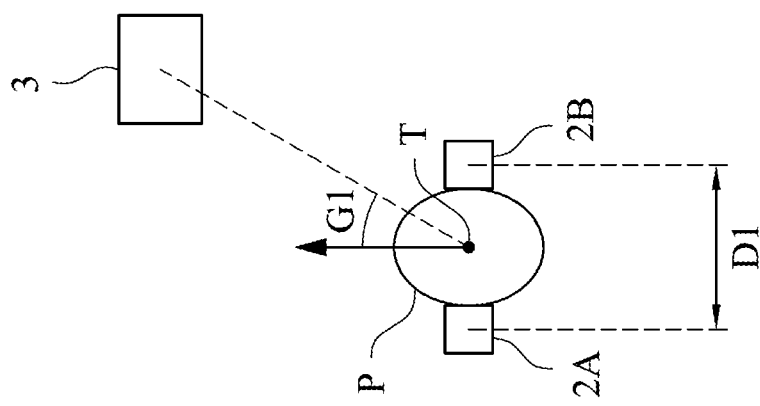

Reference is made to FIGS. 13A and 13B. FIGS. 13A and 13B illustrate schematic diagrams of different intermediate stages of method 4000 for a hearing test including the assistive listening devices 2A and 2B, the electronic device 3, and the subject P according to some embodiments of the present disclosure. In some embodiments, when the volume of the pure tone detected by the assistive listening device 2A is less than the volume of the pure tone detected by the assistive listening device 2B, the assistive listening device 2A may be configured to rotate an angle toward the electronic device 3 based on a center rotating axis T to adjust the first and second distances. As shown in FIGS. 13A and 13B, the center rotating axis T is located between the first assistive listening device 2A and the second assistive listening device 2B.

In the embodiment, when a difference between the volumes of the pure tone detected by the assistive listening device 2A and the assistive listening device 2B is in a range from about 5 dB to about 9 dB, the electronic device 3 may be configured to instruct the subject to rotate the assistive listening device 2A and the assistive listening device 2B based on the center rotating axis T by about an angle G1 through the user interface 34 and/or the sound generating unit 32. For example, the angle G1 may be about 30 degrees, but the present disclosure is not limited thereto. As such, a distance between the assistive listening device 2A and the electronic device 3 may be substantially the same as a distance between the assistive listening device 2B and the electronic device 3, and thus the assistive listening device 2A and the assistive listening device 2B may be configured to receive substantially the same volumes from the sound generating unit 32 of the electronic device 3.

Figure 14B:
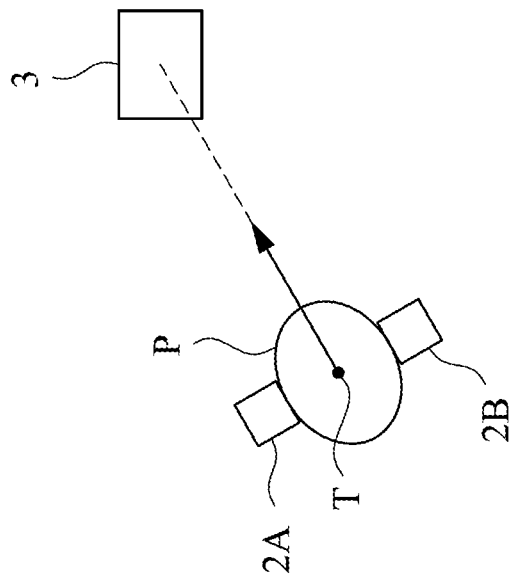
FIGS. 14A and 14B illustrate schematic diagrams of different intermediate stages of a method for a hearing test including assistive listening devices, electronic device, and a subject according to some embodiments of the present disclosure.
Figure 14A:
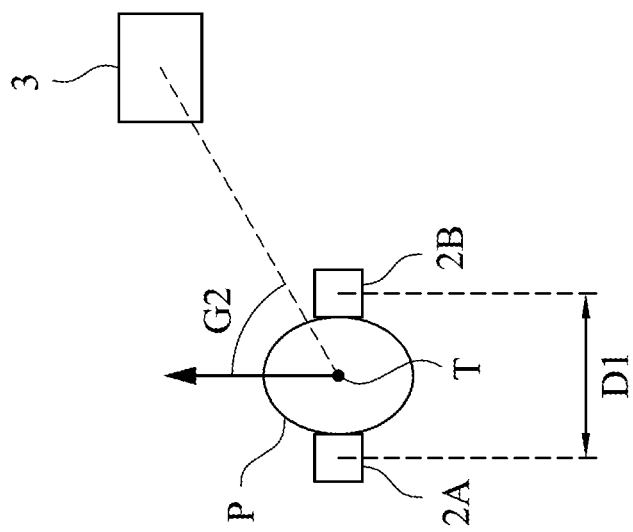

Reference is made to FIGS. 14A and 14B. FIGS. 14A and 14B illustrate schematic diagrams of different intermediate stages of method 4000 for a hearing test including the assistive listening devices 2A and 2B, the electronic device 3, and the subject P according to some embodiments of the present disclosure.

In the embodiment, when a difference between the volumes of the pure tone detected by the assistive listening device 2A and the assistive listening device 2B is in a range from about 10 dB to about 15 dB, the electronic device 3 may be configured to instruct the subject to rotate the assistive listening device 2A and the assistive listening device 2B based on the center rotating axis T by about an angle G2 through the user interface 34 and/or the sound generating unit 32. For example, the angle G2 may be about 60 degrees, but the present disclosure is not limited thereto. As such, a distance between the assistive listening device 2A and the electronic device 3 may be substantially the same as a distance between the assistive listening device 2B and the electronic device 3, and thus the assistive listening device 2A and the assistive listening device 2B may be configured to receive substantially the same volumes from the sound generating unit 32 of the electronic device 3.

Figure 15A:
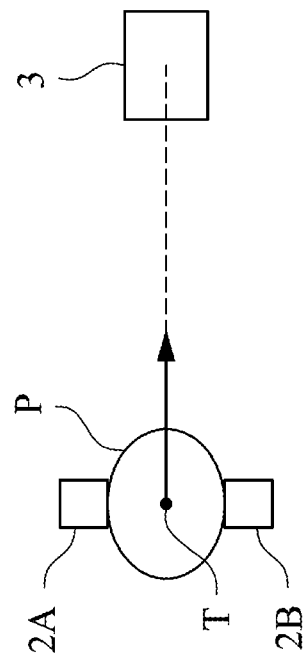
FIGS. 15A and 15B illustrate schematic diagrams of different intermediate stages of a method for a hearing test including assistive listening devices, electronic device, and a subject according to some embodiments of the present disclosure.
Figure 15B:
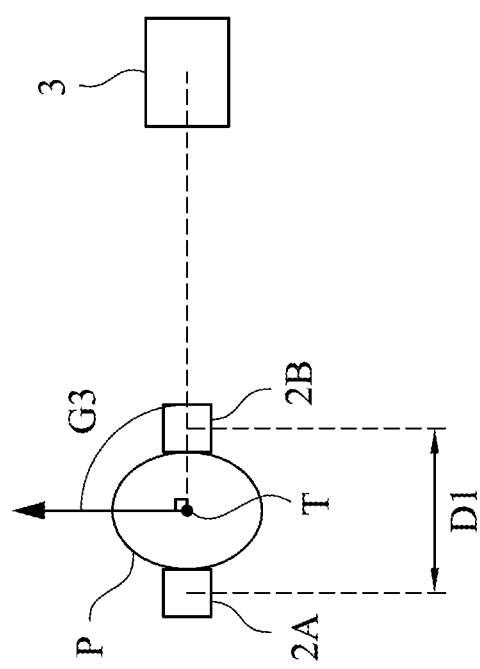

Reference is made to FIGS. 15A and 15B. FIGS. 15A and 15B illustrate schematic diagrams of different intermediate stages of method 4000 for a hearing test including the assistive listening devices 2A and 2B, the electronic device 3, and the subject P according to some embodiments of the present disclosure.

In the embodiment, when a difference between the volumes of the pure tone detected by the assistive listening device 2A and the assistive listening device 2B is greater than about 16 dB, the electronic device 3 may be configured to instruct the subject to rotate the assistive listening device 2A and the assistive listening device 2B based on the center rotating axis T by about an angle G3 through the user interface 34 and/or the sound generating unit 32. For example, the angle G3 may be about 90 degrees, but the present disclosure is not limited thereto. As such, a distance between the assistive listening device 2A and the electronic device 3 may be substantially the same as a distance between the assistive listening device 2B and the electronic device 3, and thus the assistive listening device 2A and the assistive listening device 2B may be configured to receive substantially the same volumes from the sound generating unit 32 of the electronic device 3.

In some embodiments, when a difference between the volumes of the pure tone detected by the assistive listening device 2A and the assistive listening device 2B is less than a lower limit, the electronic device 3 may be configured to instruct the subject not to rotate the assistive listening device 2A and the assistive listening device 2B through the user interface 34 and/or the sound generating unit 32, thereby maintaining the distance (or the orientation) between the assistive listening device 2A and the electronic device 3 and maintaining the distance (or the orientation) between the assistive listening device 2B and the electronic device 3 (or an angle). For example, the aforementioned lower limit may be about 4 dB, but the present disclosure is not limited thereto.

In some embodiments, after the assistive listening device 2A and the assistive listening device 2B is configured to rotate based on the center rotating axis T, a difference between the volumes of the pure tone detected by the assistive listening device 2A and the assistive listening device 2B may be still greater than the lower limit. Therefore, the electronic device 3 may be configured to instruct the subject to further rotate the assistive listening device 2A and the assistive listening device 2B based on the center rotating axis T through the user interface 34 and/or the sound generating unit 32 according to a difference between the volumes of the pure tone detected by the assistive listening device 2A and the assistive listening device 2B, such that the difference between the volumes of the pure tone detected by the assistive listening device 2A and the assistive listening device 2B may be less than the lower limit.

Reference is made to FIG. 11. Method 4000 for the hearing test then proceeds to step S4070. In step S4070, the control unit 36 of the electronic device 3 is configured to adjust an output volume of the sound generating unit 32 of the electronic device 3, such that the volumes of the testing sound detected by the assistive listening devices 2A and 2B are within the intensity region. Specifically, if the volume of the testing sound is lower than the intensity region, the control unit 36 of the electronic device 3 is configured to increase the volume of the testing sound to fall within the intensity region. Relatively, if the volume of the testing sound is higher than the intensity region, the control unit 36 of the electronic device 3 is configured to decrease the volume of the testing sound to fall within the intensity region.

Reference is made to FIG. 11. Method 4000 for the hearing test then proceeds to step S4080. In step S4080, the control unit 36 of the electronic device 3 is configured to determine whether the volume of the testing sound generated from the electronic device 3 reaches an upper volume output boundary or a lower volume output boundary of the electronic device 3. For example, when the volume of the testing sound generated from the electronic device 3 does not reach the upper volume output boundary or the lower volume output boundary of the electronic device 3, step S4010 is performed again. Relatively, when the volume of the testing sound generated from the electronic device 3 reaches the upper volume output boundary or the lower volume output boundary of the electronic device 3, the hearing test may then proceed to step S4090.

Reference is made to FIG. 11. Method 4000 for the hearing test then proceeds to step S4090. In step S4090, the electronic device 3 may be configured to instruct the subject to increase or to decrease distances between the electronic device 3 and the assistive listening devices 2A and 2B through the user interface 34 and/or the sound generating unit 32, such that the volumes of the testing sound detected by the assistive listening device 2A and the assistive listening device 2B are within the intensity region, and step S4010 is performed again.

Figure 16B:
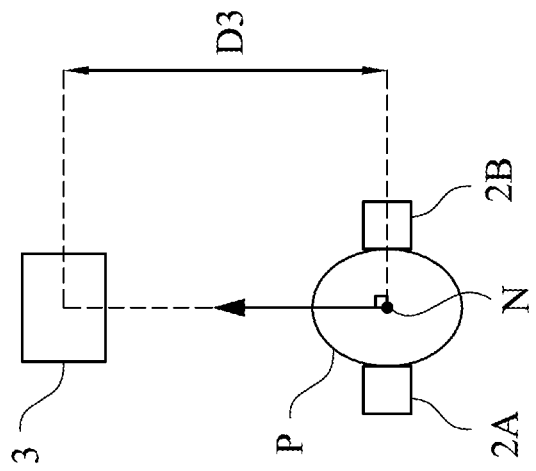
FIGS. 16A and 16B illustrate schematic diagrams of different intermediate stages of a method for a hearing test including assistive listening devices, electronic device, and a subject according to some embodiments of the present disclosure.
Figure 16A:
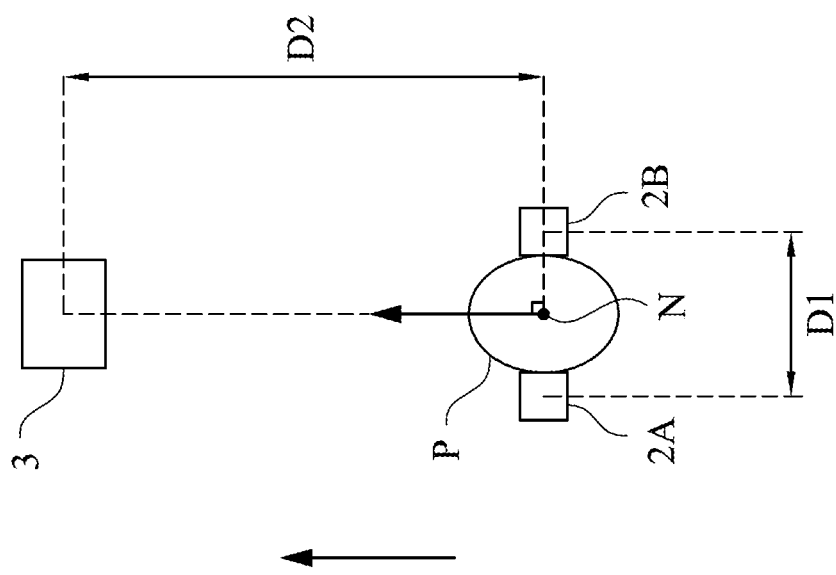

For example, reference is made to FIGS. 16A and 16B. FIGS. 16A and 16B illustrate schematic diagrams of different intermediate stages of method 4000 for a hearing test including the assistive listening devices 2A and 2B, the electronic device 3, and the subject P according to some embodiments of the present disclosure. In the embodiment, there is a position center N between the assistive listening device 2A and the assistive listening device 2B, in which a distance from the position center N to first and second assistive listening devices 2A and 2B are substantially equal, and a distance from the position center N to the first assistive listening device 2A is about half a distance between the first and second assistive listening devices 2A and 2B. A distance between the position center N and the electronic device 3 may be about a distance D2. Since the volume of the testing sound detected by at least one of the assistive listening devices 2A and 2B is less than the intensity region, the electronic device 3 may be configured to instruct the subject to decrease a distance between the position center N and the electronic device 3 to the distance D3 through the user interface 34 and/or the sound generating unit 32, such that the volumes of the testing sound detected by the assistive listening devices 2A and 2B are within the intensity region.

According to the foregoing embodiments of the disclosure, it can be seen that, a credibility of a hearing test method may be affected by a subject's improper operation of a hearing test system. Therefore, a blank stimulating sound may be selectively inserted to verify the reliability of the data of the hearing test method, thereby preventing the subject from adjusting a hearing function of an assistive listening device by using a test result with poor reliability. As such, the accuracy of the assistive listening device can be improved.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A method for determining a credibility of a hearing test, comprising:

sequentially generating a plurality of testing sounds of different volumes at each one of a plurality of frequencies for a subject;

selectively inserting a plurality of blank stimulating sounds between the testing sounds, wherein volumes of the blank stimulating sounds each equals to about zero;

receiving a plurality of feedbacks of the subject respectively corresponding to the blank stimulating sounds; and generating a credibility analysis output based on the feedbacks, wherein when a first number of the feedbacks of the heard response in the blank stimulating sounds is greater than a second number of the feedbacks of the unheard response in the blank stimulating sounds, the credibility analysis output is set to be of a poor reliability.

2. The method of claim 1, wherein the selectively inserting of the blank stimulating sounds between the testing sounds is performed such that when the feedbacks of consecutive two of the testing sounds are of the heard responses, the blank stimulating sound is set to be performed selectively after the consecutive two of the testing sounds.

3. The method of claim 1, further comprising:

responsive to a volume usage percentage for each of the frequencies, classifying each of the frequencies into a poor reliability frequency or an acceptable reliability frequency, wherein the generating of the credibility analysis output is responsive to a ratio of a first number of the reliability frequency to a second number of the acceptable reliability frequency.

4. The method of claim 3, wherein the classifying of each of the frequencies into the poor reliability frequency or the acceptable reliability frequency comprising:

calculating a third number of a plurality of designed usage volumes for each of the frequencies and further calculating a fourth number of a plurality of actual usage volumes for the each of the frequencies, when the fourth number of the actual usage volumes is greater than or equal to 80% of the third number of the designed usage volumes for a corresponding one of the frequencies, the corresponding one of the frequencies is classified as the poor reliability frequency, and when the fourth number of the actual usage volumes is less than 80% of the third number of the designed usage volumes for a corresponding one of the frequencies, the corresponding one of the frequencies is classified as the acceptable reliability frequency.

5. The method of claim 4, wherein when a fifth number of the frequencies that are of the poor reliability frequency is greater than or equal to a sixth number the frequencies that are of the acceptable reliability frequency, the credibility analysis output is set to be of a poor reliability.

* * * * *